(12) United States Patent
Renke

(10) Patent No.: US 10,820,984 B2
(45) Date of Patent: *Nov. 3, 2020

(54) IMPLANT WITH ELASTOMERIC MEMBRANE AND METHODS OF FABRICATION THEREOF

(71) Applicant: ImplantAdjust LLC, Point Roberts, WA (US)

(72) Inventor: Peter Renke, Vancouver (CA)

(73) Assignee: ImplantAdjust, LLC, Point Roberts, WA (US)

(*) Notice: Subject to any disclaimer, the term of this patent is extended or adjusted under 35 U.S.C. 154(b) by 117 days.

This patent is subject to a terminal disclaimer.

(21) Appl. No.: 16/126,232

(22) Filed: Sep. 10, 2018

(65) Prior Publication Data

US 2019/0000608 A1 Jan. 3, 2019

Related U.S. Application Data

(60) Continuation-in-part of application No. 15/133,651, filed on Apr. 20, 2016, now Pat. No. 10,070,951,
(Continued)

(51) Int. Cl.
*A61F 2/12* (2006.01)
*B29C 41/22* (2006.01)
(Continued)

(52) U.S. Cl.
CPC ............ *A61F 2/12* (2013.01); *B29C 35/0266* (2013.01); *B29C 39/10* (2013.01); *B29C 41/08* (2013.01);
(Continued)

(58) Field of Classification Search
None
See application file for complete search history.

(56) References Cited

U.S. PATENT DOCUMENTS 3,919,724 A 11/1975 Sanders et al.
4,428,364 A 1/1984 Bartolo
(Continued)

FOREIGN PATENT DOCUMENTS

CA 1121553 A 4/1982
EP 0134340 B1 11/1988
(Continued)

*Primary Examiner* — Monica A Huson
(74) *Attorney, Agent, or Firm* — The Webb Law Firm

(57) ABSTRACT

A method of forming an implant includes providing a preformed shell formed from at least one cured elastomeric layer. The preformed shell includes an outer surface, an inner surface, and an opening for accessing an interior volume of the preformed shell. The method further includes expanding the preformed shell to an expanded state, in which the interior volume is greater than the interior volume of the preformed shell at a time of forming the preformed shell and forming an inner zone having at least one inner elastomeric layer on at least a portion of the inner surface of the preformed shell, while the shell is in the expanded state, thereby forming a multi-zone shell. The method further includes reducing the interior volume of the multi-zone shell, thereby contracting the at least one inner elastomeric layer of the inner zone and causing texturing of the at least one inner elastomeric layer.

20 Claims, 20 Drawing Sheets

Related U.S. Application Data which is a division of application No. 14/079,180, filed on Nov. 13, 2013, now Pat. No. 9,351,824, application No. 16/126,232, which is a continuation-in-part of application No. PCT/US2017/028810, filed on Apr. 21, 2017.

(60) Provisional application No. 61/726,198, filed on Nov. 14, 2012, provisional application No. 62/420,134, filed on Nov. 10, 2016, provisional application No. 62/325,714, filed on Apr. 21, 2016.

(51) Int. Cl.
| | |
|---|---|
| *B29C 35/02* | (2006.01) |
| *B29C 61/00* | (2006.01) |
| *B32B 1/00* | (2006.01) |
| *B32B 27/28* | (2006.01) |
| *B32B 27/20* | (2006.01) |
| *B32B 27/08* | (2006.01) |
| *B29C 41/50* | (2006.01) |
| *B32B 3/26* | (2006.01) |
| *B29C 41/08* | (2006.01) |
| *B29C 39/10* | (2006.01) |
| *B29L 31/00* | (2006.01) |
| *B29C 73/20* | (2006.01) |
| *B29K 105/00* | (2006.01) |
| *B29K 21/00* | (2006.01) |

(52) U.S. Cl.
CPC .............. *B29C 41/22* (2013.01); *B29C 41/50* (2013.01); *B29C 61/006* (2013.01); *B32B 1/00* (2013.01); *B32B 3/266* (2013.01); *B32B 27/08* (2013.01); *B32B 27/20* (2013.01); *B32B 27/283* (2013.01); *A61F 2210/0076* (2013.01); *A61F 2240/001* (2013.01); *A61F 2250/0003* (2013.01); *A61F 2250/0004* (2013.01); *B29C 73/20* (2013.01); *B29K 2021/00* (2013.01); *B29K 2105/0058* (2013.01); *B29K 2805/00* (2013.01); *B29K 2909/00* (2013.01); *B29K 2995/0046* (2013.01); *B29K 2995/0069* (2013.01); *B29L 2031/7532* (2013.01); *B32B 2250/03* (2013.01); *B32B 2307/51* (2013.01); *B32B 2307/7265* (2013.01); *B32B 2535/00* (2013.01)

(56) References Cited

U.S. PATENT DOCUMENTS

| | | |
|---|---|---|
| 4,574,780 A | 3/1986 | Manders |
| 4,636,213 A | 1/1987 | Pakiam |
| 4,650,487 A | 3/1987 | Chaglassian |
| 4,671,255 A | 6/1987 | Dubrul et al. |
| 4,685,447 A | 8/1987 | Iversen et al. |
| 4,738,657 A | 4/1988 | Hancock et al. |
| 4,798,584 A | 1/1989 | Hancock et al. |
| 4,944,749 A | 7/1990 | Becker |
| 4,955,909 A | 9/1990 | Ersek et al. |
| 4,960,425 A | 10/1990 | Yan et al. |
| 5,066,303 A | 11/1991 | Bark et al. |
| 5,282,857 A | 2/1994 | Perry et al. |
| 5,376,323 A | 12/1994 | Eaton |
| 5,383,929 A | 1/1995 | Ledergerber |
| 5,447,535 A | 9/1995 | Muller |
| 5,496,367 A | 3/1996 | Fisher |
| 5,525,275 A | 6/1996 | Iversen et al. |
| 5,545,221 A | 8/1996 | Hang-Fu |
| 5,571,179 A | 11/1996 | Manders et al. |
| 5,630,844 A | 5/1997 | Dogan et al. |
| 5,662,708 A | 9/1997 | Hayes et al. |
| 5,683,420 A | 11/1997 | Jeter et al. |
| 5,695,338 A | 12/1997 | Robert |
| 5,803,746 A | 9/1998 | Barrie et al. |
| 5,935,164 A | 8/1999 | Iversen |
| 5,964,806 A | 10/1999 | Cook et al. |
| 6,060,639 A | 5/2000 | Petrick |
| 6,066,220 A | 5/2000 | Schneider-Nieskens |
| 6,146,419 A | 11/2000 | Eaton |
| 6,156,065 A | 12/2000 | Eaton |
| 6,187,043 B1 | 2/2001 | Ledergerber |
| 6,315,796 B1 | 11/2001 | Eaton |
| 6,520,989 B1 | 2/2003 | Eaton |
| 6,602,452 B2 | 8/2003 | Schuessler |
| 6,743,254 B2 | 6/2004 | Guest et al. |
| 6,755,861 B2 | 6/2004 | Nakao |
| 6,780,366 B2 | 8/2004 | Vang et al. |
| 6,783,546 B2 | 8/2004 | Zucherman et al. |
| 6,802,861 B1 | 10/2004 | Hamas |
| 7,081,136 B1 | 7/2006 | Becker et al. |
| 7,226,463 B2 | 6/2007 | Gedebou |
| 7,364,540 B1 | 4/2008 | Burton et al. |
| 7,628,604 B2 | 12/2009 | Schuessler |
| 7,645,475 B2 | 1/2010 | Prewett |
| 7,651,483 B2 | 1/2010 | Byrum et al. |
| 7,678,604 B2 | 3/2010 | Kim |
| 7,731,700 B1 | 6/2010 | Schytte |
| 7,762,999 B2 | 7/2010 | Byrum |
| 7,878,075 B2 | 2/2011 | Johansson et al. |
| 8,070,674 B1 | 12/2011 | Hughes |
| 8,206,450 B2 | 6/2012 | Henry et al. |
| 8,349,007 B2 | 1/2013 | Berg et al. |
| 8,377,127 B2 | 2/2013 | Schuessler |
| 8,398,710 B2 | 3/2013 | Forsell |
| 8,431,179 B2 | 4/2013 | Judge et al. |
| 8,506,627 B2 | 8/2013 | Van Epps et al. |
| 8,911,765 B2 | 12/2014 | Moses et al. |
| 9,138,310 B2 | 9/2015 | Powell et al. |
| 9,351,824 B2 | 5/2016 | Renke |
| 9,688,006 B2 | 6/2017 | Nieto et al. |
| 10,070,951 B2 * | 9/2018 | Renke ................. B29C 35/0266 |
| 2002/0151763 A1 | 10/2002 | Cook et al. |
| 2004/0254625 A1 | 12/2004 | Stephens et al. |
| 2005/0283119 A1 | 12/2005 | Uth et al. |
| 2006/0224239 A1 | 10/2006 | Tiahrt |
| 2006/0281964 A1 | 12/2006 | Burton et al. |
| 2006/0293626 A1 | 12/2006 | Byrum et al. |
| 2007/0050027 A1 | 3/2007 | McGhan et al. |
| 2007/0233273 A1 | 10/2007 | Connell |
| 2008/0167518 A1 | 7/2008 | Burton et al. |
| 2009/0264901 A1 | 10/2009 | Franklin et al. |
| 2010/0049316 A1 | 2/2010 | Schuessler |
| 2010/0114311 A1 | 5/2010 | Becker |
| 2010/0204792 A1 | 8/2010 | Greco |
| 2011/0196195 A1 | 8/2011 | Raven et al. |
| 2011/0270391 A1 | 11/2011 | Chitre et al. |
| 2011/0288639 A1 | 11/2011 | Trilokekar et al. |
| 2011/0306827 A1 | 12/2011 | Chitre et al. |
| 2012/0078284 A1 | 3/2012 | Jones et al. |
| 2012/0123537 A1 | 5/2012 | Manesis et al. |
| 2012/0277524 A1 | 11/2012 | Franklin et al. |
| 2012/0277858 A1 | 11/2012 | Brinon |
| 2013/0116784 A1 | 5/2013 | Hamas et al. |
| 2013/0131799 A1 | 5/2013 | Schuessler |
| 2013/0231743 A1 | 9/2013 | Becker |
| 2015/0282927 A1 | 10/2015 | Van Epps et al. |

FOREIGN PATENT DOCUMENTS

| | | |
|---|---|---|
| EP | 0181720 B1 | 5/1990 |
| EP | 0412703 A1 | 2/1991 |
| EP | 0422302 B1 | 9/1993 |
| EP | 1229857 B1 | 12/2005 |
| EP | 0996389 B1 | 2/2008 |
| EP | 1736199 B1 | 2/2009 |
| EP | 1189552 B1 | 4/2009 |
| EP | 1736202 B1 | 7/2009 |
| EP | 1815881 B1 | 11/2009 |
| EP | 2554138 A1 | 2/2013 |
| EP | 1736196 B2 | 6/2013 |
| FR | 2953122 A1 | 6/2011 |

(56) References Cited

FOREIGN PATENT DOCUMENTS

| GB | 2151927 A | 7/1985 |
|---|---|---|
| JP | 3140155 A | 6/1991 |
| WO | 9705832 A1 | 2/1997 |
| WO | 9856311 A1 | 12/1998 |
| WO | 0066030 A1 | 11/2000 |
| WO | 0069374 A1 | 11/2000 |
| WO | 0126581 A1 | 4/2001 |
| WO | 0152774 A2 | 7/2001 |
| WO | 03008493 A2 | 1/2003 |
| WO | 03065940 A1 | 8/2003 |
| WO | 2004066812 A2 | 8/2004 |
| WO | 2004112656 A2 | 12/2004 |
| WO | 2005084586 A1 | 9/2005 |
| WO | 2009129474 A1 | 10/2009 |
| WO | 2010022131 A1 | 2/2010 |
| WO | 2011058550 A1 | 5/2011 |
| WO | 2011097292 A1 | 8/2011 |
| WO | 2011097451 A1 | 8/2011 |
| WO | 2012064683 A1 | 5/2012 |
| WO | 2012154948 A1 | 11/2012 |
| WO | 2012154952 A1 | 11/2012 |
| WO | 2013058878 A1 | 4/2013 |

\* cited by examiner

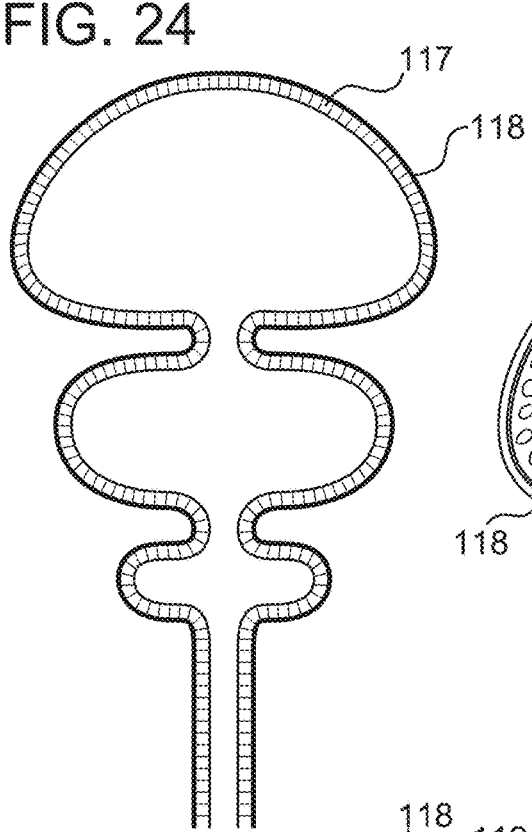
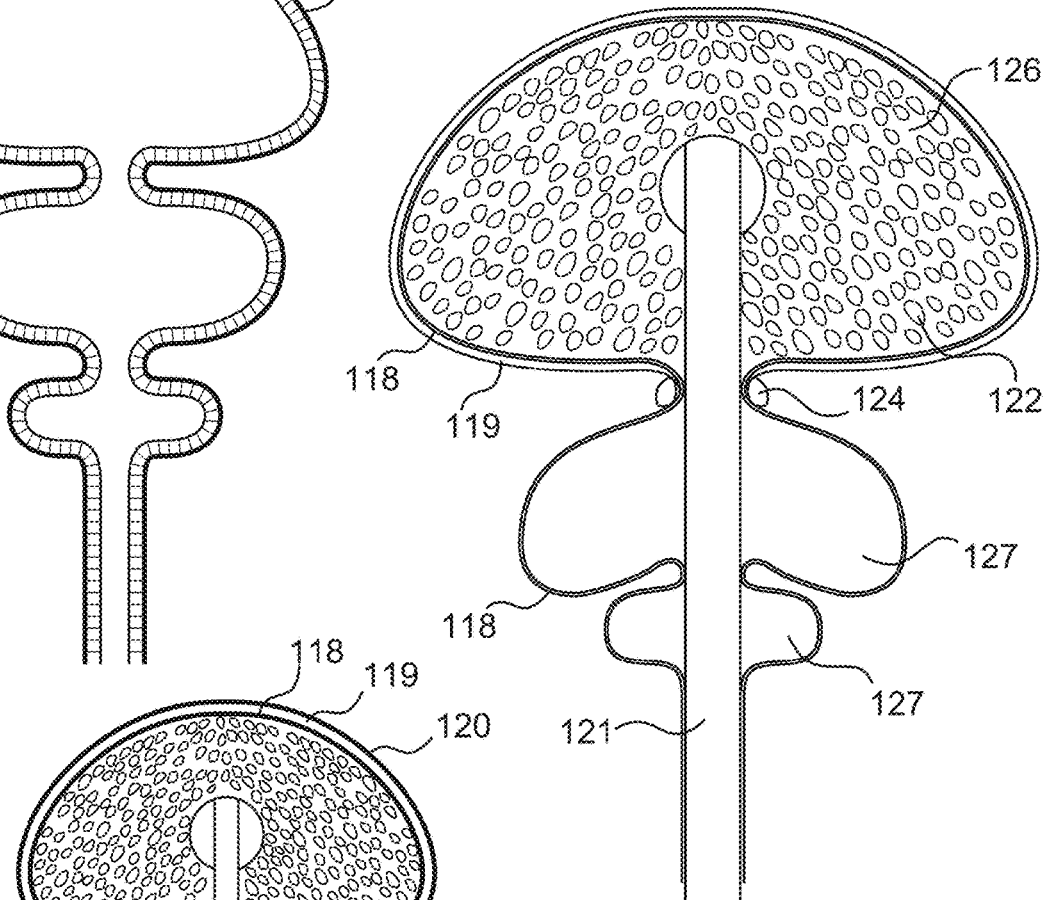
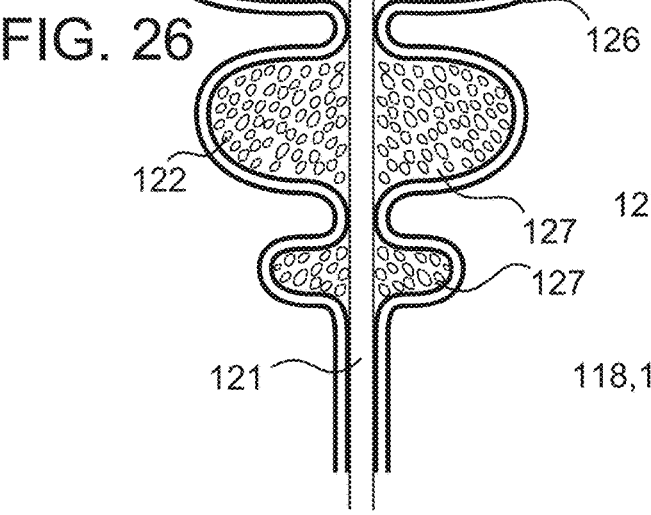
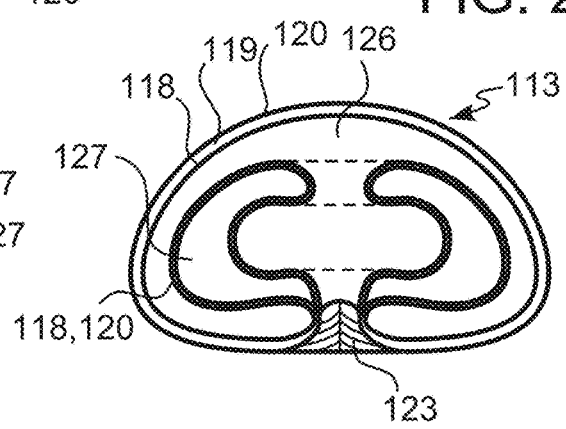

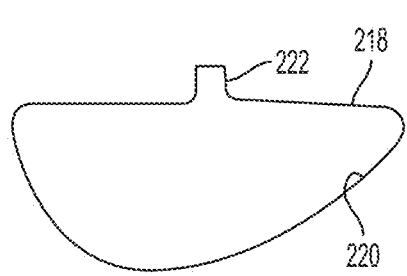
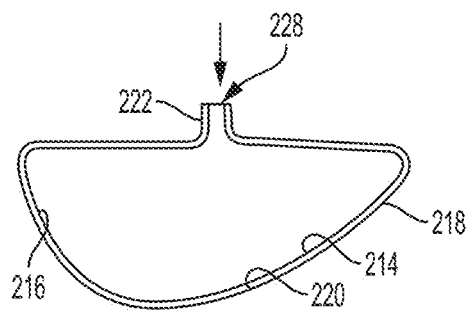
FIG. 32A     FIG. 32B
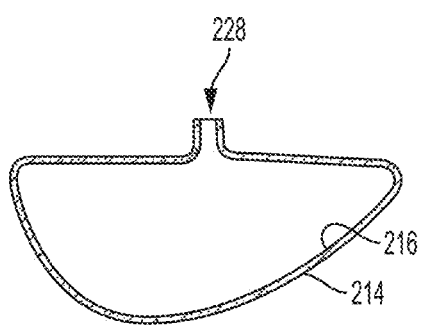
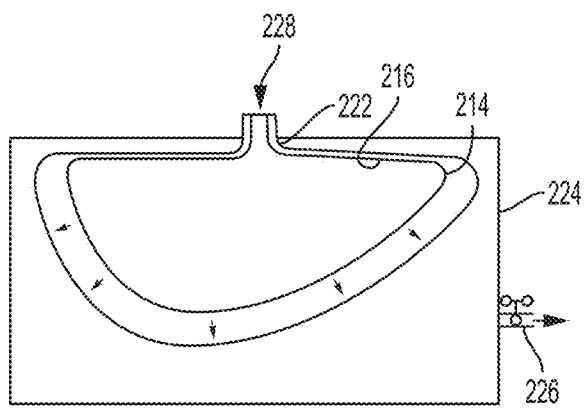
FIG. 32C     FIG. 32D
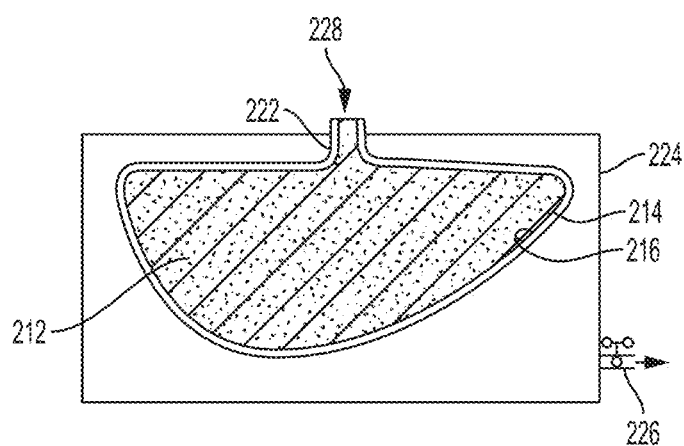
FIG. 32E

IMPLANT WITH ELASTOMERIC MEMBRANE AND METHODS OF FABRICATION THEREOF

CROSS-REFERENCE TO RELATED APPLICATIONS

This application is a continuation-in-part of U.S. patent application Ser. No. 15/133,651, filed Apr. 20, 2016, which is a divisional of U.S. patent application Ser. No. 14/079, 180, filed Nov. 13, 2013, which issued as U.S. Pat. No. 9,351,824 on May 31, 2016, which claims priority to U.S. Provisional Patent Application No. 61/726,198, filed Nov. 14, 2012, each of which is hereby incorporated by reference in its entirety.

Also, this application is also a continuation-in-part of International Patent Application No. PCT/US2017/028810, filed Apr. 21, 2017, which claims priority to U.S Provisional Patent Application No. 62/420,134 filed Nov. 10, 2016, and U.S. Provisional Patent Application No. 62/325,714 filed Apr. 21, 2016, each of which is hereby incorporated by reference in its entirety.

BACKGROUND OF THE INVENTION

Field of the Invention

This invention generally relates to implant prosthetics and methods of fabrication thereof and, in particular, to implants having an elastomeric membrane or shell with textured inner and/or outer surfaces.

Description of Related Art

Many breast implants are commercially available. A single chamber design is most common and is available in a variety of fixed volumes to produce a range of sizes and shape characteristics from about 80 to 800 cubic centimeters. As used herein, "chamber" refers to the interior portion of a breast implant, which is enclosed by an outer shell or membrane. As is known by those skilled in the art, the interior portion of an implant may also be referred to as a lumen. Implants are generally filled with silicone gel or saline. Viscoelastic silicone shells of implants can be similar in composition, but vary in thickness, texture, and surface treatments. There are also significant differences with respect to the filling materials. The silicone gel implants generally have more natural properties, with fewer noticeable edges and rippling effects. The viscosity of the silicone gel reduces fluid motion that results in these beneficial properties. The silicone gel filling the implant may alter over time to become firmer, softer, and change in elasticity, depending on its composition. Historically, a major complication has been gel bleed leading to capsular contraction and tissue toxicity to the patient. Many gel-filled implants have additional barrier coatings or layers to lessen the diffusion of silicone into the tissues. Diffusion can be reduced, but not eliminated.

Saline implants were developed to eliminate complications related to fluid bleed. Saline is biocompatible and able to be absorbed without tissue toxicity complications in the event of a slow bleed or rupture of the implant. The low viscosity of saline allows for significant fluid motion leading to deformation of the fluid-filled shell. The wave and ripple motion is often visible through the overlying tissue. This is a more significant complication in cases where there are not significant amounts of tissue surrounding the implant. The deformation of the viscoelastic membrane can cause the surrounding tissue to scar and contract, distorting and hardening the feel of the implant. Saline implants are often placed deep under muscle tissue of the chest and slightly overfilled to prevent complications.

Shell coatings and texturing have been developed to reduce capsular contraction, with reasonable success. For example, variable surface treatments can work by enabling tissues to adhere and distribute forces responsible for contracture. The materials utilized to form, coat, and fill the implants have resulted in a wide variety of available designs. Size and shape alone produce many options. The designs become more involved when multi-chamber and variable volumetric designs are considered. Variability of volume during surgery allows for adjustments to be made for general size and symmetry. Access ports and valves are used to inflate or deflate the implant. In some cases, the filling tube is left in place for a short period to allow for further adjustments post-surgery. This adjustability is a desirable and, often, a necessary feature in the case of tissue expanders.

Multi-chamber implants predominantly consist of an inner chamber and an outer chamber filled with silicone, saline, or a combination thereof. The combination of chambers allows for greater variability in size and shape characteristics. Currently available models have a double membrane, double chamber design, in which an outer chamber has a fixed volume of gel and an adjustable inner chamber is filled with saline. These implants provide a natural appearance and feel with the added advantage of temporary adjustability. However, these more complex designs have been found to be less resistant to shear forces in areas where there are junctions between the membranes and valve port.

An exemplary implant formed from an elastomeric shell with a textured exterior surface is disclosed in U.S. Pat. No. 8,506,627 to Van Epps et al. The implant disclosed in the '627 patent includes a textured fixation region on an anterior face of the shell. The fixation region can have a different texture from other portions of the exterior surface of the shell. In some examples, the shell of the implant is formed over a mandrel. For example, the mandrel can be repeatedly dipped into a flowable silicon elastomer until a membrane of desired thickness is formed. Portions of the exterior surface of the membrane can be subjected to a texturing process in which granulated solid particles (e.g., salt crystals) are applied over portions of the exterior surface of the membrane to form the fixation surface. After the textured surface stabilizes, the granulated solid particles can be removed by, for example, immersing the membrane in a fluidized bath (e.g., an aqueous salt bath) to dissolve the particles, resulting in a membrane with a textured surface resembling a plurality of crystalline particles.

However, there is a continuing need to develop implants that safely provide a natural feel and appearance when surgically implanted. For example, implants should adhere and/or interact with breast or other body tissues in a biocompatible and effective manner Further, implant designs with improved biocompatibility and/or which can be manufactured more easily and efficiently are needed. The implants and methods of formation thereof provided herein are provided to address some or all of these needs.

SUMMARY OF THE INVENTION

According to a preferred and non-limiting embodiment or aspect, an adjustable implant is provided. The adjustable implant comprises an elastomeric membrane enclosed or partially enclosed about a chamber, which is adapted to expand when filled with a fluid. The membrane comprises: an outer zone formed from at least one outer elastomeric layer, the outer zone comprising an exterior surface having at least one molded textured portion thereon; and an inner zone formed from at least one elastomeric middle layer positioned on an inner surface of the outer zone. The implant is configured such that the inner zone is under contraction from a contracting force provided by the outer zone.

According to another preferred and non-limiting embodiment or aspect, a method of forming an implant is provided. The method comprises: forming an outer zone of an elastomeric membrane comprising at least one elastomeric layer by casting in a mold, wherein an inner surface of the mold comprises one or more textured portions, which are molded onto an exterior surface of the at least one elastomeric layer to form one or more molded textured portions. The method further comprises: expanding the outer zone, such that a volume enclosed by the outer zone is expanded; forming an inner zone comprising one or more elastomeric layers in the expanded outer zone; retracting the outer zone and the inner zone to a retracted state; and forming an adjustable implant from the membrane by enclosing the membrane to form at least one chamber.

According to another preferred and non-limiting embodiment or aspect, an implant for volumetrically altering, replacing, expanding, or augmenting tissues is provided. The implant includes an enclosed or partially enclosed elastomeric membrane formed from one or more laminated elastomeric layers. The membrane defines an interior volume. The implant also includes a cohesive gel disposed in the interior volume of the elastomeric membrane. A volume of the cohesive gel is greater than a volume enclosed by the elastomeric membrane at the time of curing, thereby causing the elastomeric membrane to exert a contracting force on the cohesive gel.

According to another preferred and non-limiting embodiment or aspect, a method of forming an implant for volumetrically altering, replacing, expanding, or augmenting tissues is provided. The method includes: forming an elastomeric membrane having one or more laminated elastomeric layers, the membrane enclosing or partially enclosing an interior volume; expanding the elastomeric membrane, such that the interior volume enclosed or partially enclosed by the elastomeric membrane is expanded; filling the elastomeric membrane with a flowable elastomeric material; and curing the elastomeric material to form a cohesive gel.

According to another preferred and non-limiting aspect or embodiment, a method of forming an implant for volumetrically altering, replacing, expanding, or augmenting body tissues including an elastomeric membrane at least partially enclosing an interior volume is provided. The method includes: forming an outer zone of the elastomeric membrane by casting in a mold, the outer zone comprising at least one elastomeric layer, wherein an inner surface of the mold comprises one or more textured portions, which are molded onto an exterior surface of the outer zone, thereby forming one or more molded textured portions on the exterior surface of the outer zone. The method further includes expanding the outer zone, thereby increasing a volume enclosed by the outer zone and forming an expanded zone of the elastomeric membrane comprising at least one elastomeric layer on an inner surface of the outer zone. The expanded zone at least partially encloses a volume at the time of forming, which is greater than a volume enclosed by the outer zone at the time of forming the outer zone. The method further includes forming an adjustable implant from the elastomeric membrane by enclosing the interior volume, wherein the exterior surface of the implant comprises one or more molded textured portions.

According to another preferred and non-limiting embodiment or aspect, an implant for volumetrically altering, replacing, expanding, or augmenting tissues is provided. The implant includes: an enclosed or partially enclosed elastomeric membrane formed from a plurality of laminated elastomeric layers. The membrane defines an interior volume. The implant further includes a cohesive gel disposed in the interior volume of the elastomeric membrane. A volume of the cohesive gel is greater than a volume enclosed by the elastomeric membrane at the time of curing the elastomeric membrane, thereby causing the elastomeric membrane to exert a contracting force on the cohesive gel. An exterior surface of the elastomeric membrane comprises at least one textured portion having a texture pattern different from other portions of the exterior surface of the elastomeric membrane.

According to another preferred and non-limiting aspect or embodiment, a method of forming an implant for volumetrically altering, replacing, expanding, or augmenting body tissues includes providing a preformed shell formed from at least one cured elastomeric layer. The preformed shell includes an outer surface, an inner surface, and an opening for accessing an interior volume of the preformed shell. The method also includes expanding the preformed shell to an expanded state, in which the interior volume is greater than the interior volume of the preformed shell at a time of forming the preformed shell, and forming an inner zone having at least one inner elastomeric layer on at least a portion of the inner surface of the preformed shell, while the shell is in the expanded state, thereby forming a multi-zone shell. The method further includes reducing the interior volume of the multi-zone shell, thereby contracting the at least one inner elastomeric layer of the inner zone and causing texturing of the at least one inner elastomeric layer, followed by forming the implant by enclosing the multi-zone shell to form at least one chamber.

According to another preferred and non-limiting aspect or embodiment, a method of forming an implant for volumetrically altering, replacing, expanding, or augmenting body tissues includes providing a preformed shell formed from at least one cured elastomeric layer. The preformed shell includes an outer surface, an inner surface, and an opening for accessing an interior volume of the preformed shell. The method further includes placing the preformed shell on a mandrel to expand the preformed shell to an expanded state in which the interior volume of the preformed shell is greater than a volume of the preformed shell at a time of forming the preformed shell. While the preformed shell is on the mandrel, an outer zone having at least one outer elastomeric layer is formed on at least a portion of the outer surface of the preformed shell, while the preformed shell is in the expanded state, to form a multi-zone shell. The method further includes placing the multi-zone shell on a mandrel in an inverted orientation, in which the outer zone of the multi-zone shell contacts the mandrel and forming an inner zone having at least one inner elastomeric layer on at least a portion of an inner surface of the multi-zone shell, while the multi-zone shell is on the mandrel and in the expanded state. Next, the method includes reducing the interior volume of the multi-zone shell by removing the multi-zone shell from the mandrel, thereby contracting the at least one outer elastomeric layer and the at least one inner elastomeric layer. The method further includes causing texturing of the at least one outer elastomeric layer and the at least one inner elastomeric layer; and forming the implant by enclosing the shell to form at least one chamber.

According to another preferred and non-limiting aspect or embodiment, an implant for volumetrically altering, replacing, expanding, or augmenting tissues includes an enclosed or partially enclosed elastomeric shell formed from a plurality of laminated elastomeric layers defining an interior volume; and a cohesive gel disposed in the interior volume of the elastomeric shell. The elastomeric shell includes: a preformed shell comprising at least one elastomeric layer having an inner surface and an outer surface; an outer zone having at least one outer elastomeric layer covering at least a portion of the outer surface of the preformed shell; and an inner zone having at least one inner elastomeric layer covering at least a portion of the inner surface of the preformed shell. A volume enclosed by the outer zone and the inner zone at the time of forming the outer zone and the inner zone is greater than a volume of the preformed shell at a time of forming the preformed shell.

Further preferred and non-limiting embodiments or aspects of the present invention will now be described in the following numbered clauses:

Clause 1: A method of forming an implant for volumetrically altering, replacing, expanding, or augmenting body tissues comprising an elastomeric membrane at least partially enclosing an interior volume, the method comprising: forming an outer zone of the elastomeric membrane by casting in a mold, the outer zone comprising at least one elastomeric layer, wherein an inner surface of the mold comprises one or more textured portions which are molded onto an exterior surface of the outer zone, thereby forming one or more molded textured portions on the exterior surface of the outer zone; expanding the outer zone, thereby increasing a volume enclosed by the outer zone; forming an expanded zone of the elastomeric membrane comprising at least one elastomeric layer on an inner surface of the outer zone, the expanded zone at least partially enclosing a volume at the time of forming which is greater than a volume enclosed by the outer zone at the time of forming the outer zone; and forming an adjustable implant from the elastomeric membrane by enclosing the interior volume, wherein the exterior surface of the implant comprises one or more molded textured portions.

Clause 2: The method of clause 1, further comprising retracting the elastomeric membrane to a retracted state prior to forming the implant from the elastomeric membrane, wherein the volume enclosed by the outer zone in the retracted state is greater than the volume enclosed by the outer zone at the time of forming the outer zone, such that the molded textured portions of the implant are expanded compared to the one or more textured portions of the inner surface of the mold.

Clause 3: The method of clause 1 or clause 2, wherein expanding the outer zone comprises expanding a volume enclosed by the outer zone by between 10% and 500% compared to the volume enclosed by the outer zone when formed.

Clause 4: The method of any of clauses 1-3, wherein the inner surface of the mold comprises at least a first molded textured portion having a first texture pattern and at least a second molded textured portion having a second texture pattern, and wherein the exterior surface of the implant comprises a portion having the first texture pattern and a portion having the second texture pattern.

Clause 5: The method of clause 4, wherein at least one of the textured portions on the inner surface of the mold is configured to provide an adhesion region for improving adhesion with surrounding body tissues.

Clause 6: The method of clause 4 or clause 5, wherein the inner surface of the mold further comprises one or more substantially flat portions separating the textured portions.

Clause 7: The method of any of clauses 1-6, wherein forming the expanded zone comprises forming a plurality of laminated elastomeric layers of variable hardness.

Clause 8: The method of clause 7, wherein an innermost layer of the plurality of layers is softer than an outermost layer of the plurality of layers.

Clause 9: The method of clause 8, wherein the innermost layer of the plurality of layers has a hardness of between about Shore 00-10 and about Shore A-20, and wherein the outermost layer of the plurality of layers has a hardness of between about Shore A-20 and Shore A-40.

Clause 10: The method of any of clauses 1-9, further comprising pre-stressing the at least one elastomeric layer of the outer zone prior to expanding the outer zone.

Clause 11: The method of any of clauses 1-10, wherein forming the outer zone comprises introducing a flowable elastomeric material to the inner surface of the mold and curing the material to form the at least one elastomeric layer.

Clause 12: The method of any of clauses 1-11, further comprising filling the interior volume defined by the elastomeric membrane with a flowable elastomeric material and curing the flowable elastomeric material to form a cohesive gel.

Clause 13: The method of clause 12, wherein the cohesive gel is bonded to an interior surface of the elastomeric membrane.

Clause 14: The method of clause 12, wherein a volume of the cohesive gel when cured is between about 5% and 50% larger than a volume enclosed by the outer zone at the time of forming.

Clause 15: The method of any of clauses 1-14, wherein the mold comprises a volumetrically expandable mold, and wherein an interior volume of the mold is increased to cause the expansion of the at least one elastomeric layer of the outer zone.

Clause 16: The method of any of clauses 1-15, wherein the mold comprises a plastic single-use disposable mold.

Clause 17: The method of any of clauses 1-16, wherein the at least one elastomeric layer of the outer zone has Shore hardness of about Shore A-10 to A-40, and preferably about Shore A-20 to Shore A-30.

Clause 18: The method of any of clauses 1-17, wherein the molded textured portion comprises at least one of the following: channels, ridges, protrusions, granulated or crystalline structures, cross-hatches, waves, or any combination thereof.

Clause 19: The method of any of clauses 1-18, wherein the molded textured portion comprises molded guidelines for assisting in surgical placement of the implant relative to the body tissue to be altered, expanded, or augmented.

Clause 20: An implant for volumetrically altering, replacing, expanding, or augmenting tissues, comprising: an enclosed or partially enclosed elastomeric membrane formed from a plurality of laminated elastomeric layers, the membrane defining an interior volume; and a cohesive gel disposed in the interior volume of the elastomeric membrane, wherein a volume of the cohesive gel is greater than a volume enclosed by the elastomeric membrane at the time of curing the elastomeric membrane, thereby causing the elastomeric membrane to exert a contracting force on the cohesive gel, and wherein an exterior surface of the elastomeric membrane comprises at least one textured portion having a texture pattern different from other portions of the exterior surface of the elastomeric membrane.

Clause 21: The implant of clause 20, wherein the plurality of laminated elastomeric layers comprise elastomeric layers of variable hardness.

Clause 22: The implant of clause 20 or clause 21, wherein an innermost layer of the plurality of layers is softer than an outermost layer of the plurality of layers.

Clause 23: The implant of any of clauses 20-22, wherein the innermost layer of the plurality of layers has a hardness of between about Shore 00-10 and about Shore A-20, and wherein the outermost layer of the plurality of layers has a hardness of between about Shore A-20 and Shore A-40.

Clause 24: The implant of any of clauses 20-23, wherein the volume of the cohesive gel when cured is between about 5% and about 50% larger than a volume enclosed or partially enclosed by the elastomeric membrane at the time of curing.

Clause 25: A method of forming an implant for volumetrically altering, replacing, expanding, or augmenting body tissues, the method comprising: providing a preformed shell formed from at least one cured elastomeric layer, the preformed shell comprising an outer surface, an inner surface, and an opening for accessing an interior volume of the preformed shell; expanding the preformed shell to an expanded state, in which the interior volume is greater than the interior volume of the preformed shell at a time of forming the preformed shell; forming an inner zone comprising at least one inner elastomeric layer on at least a portion of the inner surface of the preformed shell, while the shell is in the expanded state, thereby forming a multi-zone shell; reducing the interior volume of the multi-zone shell, thereby contracting the at least one inner elastomeric layer of the inner zone and causing texturing of the at least one inner elastomeric layer; and forming the implant by enclosing the multi-zone shell to form at least one chamber.

Clause 26: The method of clause 25, wherein expanding the preformed shell to an expanded state comprises inverting the preformed shell and placing the inverted preformed shell on a mandrel, such that the outer surface of the shell contacts a surface of the mandrel.

Clause 27: The method of clause 26, wherein a volume enclosed by the surface of the mandrel is greater than the interior volume of the preformed shell at the time of forming the preformed shell.

Clause 28: The method of clause 25 or clause 26, wherein reducing the interior volume of the multi-zone shell comprises removing the multi-zone shell from the mandrel and returning the multi-zone shell to a non-inverted orientation.

Clause 29: The method of any of clauses 25-27, wherein expanding the preformed shell comprises expanding the interior volume of the preformed shell by between 50% and 800% compared to the volume of the preformed shell at the time of forming the preformed shell.

Clause 30: The method of any of clauses 25-29, wherein forming the inner zone comprises, while the preformed shell is in the expanded state, forming a plurality of laminated inner elastomeric layers of variable hardness on the inner surface of the preformed shell.

Clause 31: The method of clause 30, wherein a proximal-most layer of the plurality of inner elastomeric layers and a distal-most layer of the plurality of inner elastomeric layers are firmer than middle layers of the plurality of inner elastomeric layers.

Clause 32: The method of any of clauses 25-31, wherein the proximal-most layer and the distal-most layer of the plurality of inner elastomeric layers are formed by blending elastomeric materials having a hardness of up to Shore A-20, and wherein the middle layers of the plurality of inner elastomeric layers have a hardness of between about Shore 00-10 and Shore A-10.

Clause 33: The method of any of clauses 25-32, wherein forming the implant comprising filling the interior volume of the multi-zone shell with a flowable elastomeric material and curing the flowable elastomeric material to form a cohesive gel.

Clause 34: The method of clause 33, wherein the cohesive gel is bonded the texturing of the at least one inner elastomeric layer.

Clause 35: The method of clause 34, wherein a volume of the cohesive gel when cured is between about 5% and 50% larger than a volume enclosed by the preformed shell at the time of forming the preformed shell.

Clause 36: The method of any of clauses 25-35, further comprising forming an outer zone comprising at least one outer elastomeric layer covering at least a portion of the outer surface of the preformed shell, while the preformed shell is in the expanded state and prior to forming the inner zone.

Clause 37: The method of clause 36, further comprising reducing the interior volume of the preformed shell after forming the outer zone, which causes texturing of the at least one outer elastomeric layer of the outer zone.

Clause 38: The method of clause 37, wherein the texturing of the outer zone is configured to provide an adhesion region for improving adhesion with surrounding body tissues.

Clause 39: The method of any of clauses 36-38, wherein the outer zone comprises a plurality of outer elastomeric layers of variable hardness ranging from about Shore 00-30 to Shore A20.

Clause 40: The method of any of clauses 36-39, wherein forming the outer zone comprises placing the preformed shell on a mandrel, such that the inner surface of the preformed shell contacts the surface of the mandrel, and applying the at least one outer elastomeric layer to the outer surface of the preformed shell.

Clause 41: The method of clause 40, wherein a volume enclosed by the mandrel is greater than the volume of the preformed shell, at the time of forming the preformed shell.

Clause 42: A method of forming an implant for volumetrically altering, replacing, expanding, or augmenting body tissues, the method comprising: providing a preformed shell formed from at least one cured elastomeric layer, the preformed shell comprising an outer surface, an inner surface, and an opening for accessing an interior volume of the preformed shell; placing the preformed shell on a mandrel to expand the preformed shell to an expanded state in which the interior volume of the preformed shell is greater than a volume of the preformed shell at a time of forming the preformed shell; while the preformed shell is on the mandrel, forming an outer zone comprising at least one outer elastomeric layer on at least a portion of the outer surface of the preformed shell, while the preformed shell is in the expanded state, to form a multi-zone shell; placing the multi-zone shell on a mandrel in an inverted orientation, in which the outer zone of the multi-zone shell contacts the mandrel; forming an inner zone comprising at least one inner elastomeric layer on at least a portion of an inner surface of the multi-zone shell, while the multi-zone shell is on the mandrel and in the expanded state; reducing the interior volume of the multi-zone shell by removing the multi-zone shell from the mandrel, thereby contracting the at least one outer elastomeric layer and the at least one inner elastomeric layer, and causing texturing of the at least one outer elastomeric layer and the at least one inner elastomeric layer; and forming the implant by enclosing the shell to form at least one chamber.

Clause 43: An implant for volumetrically altering, replacing, expanding, or augmenting tissues, comprising: an enclosed or partially enclosed elastomeric shell formed from a plurality of laminated elastomeric layers, the elastomeric shell defining an interior volume; and a cohesive gel disposed in the interior volume of the elastomeric shell, wherein the elastomeric shell comprises: a preformed shell comprising at least one elastomeric layer, the preformed portion having an inner surface and an outer surface; an outer zone comprising at least one outer elastomeric layer covering at least a portion of the outer surface of the preformed shell; and an inner zone comprising at least one inner elastomeric layer covering at least a portion of the inner surface of the preformed shell, wherein a volume enclosed by the outer zone and the inner zone at the time of forming the outer zone and the inner zone is greater than a volume of the preformed shell at a time of forming the preformed shell.

Clause 44: The implant of clause 43, wherein a volume enclosed by the outer zone and the inner zone of the implant is less than the volume enclosed by the outer zone and the inner zone at the time of forming the outer zone and the inner zone, such that the preformed shell exerts a contracting force on the inner zone and the outer zone, which causing texturing of the inner zone and the outer zone.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

Some of the advantages and features of the preferred embodiments of the invention have been summarized herein above. These embodiments along with other potential embodiments of the device will become apparent to those skilled in the art when referencing the following drawings in conjunction with the detailed descriptions as they relate to the figures.

FIG. 24 is a cross-sectional view of a casting mandrel for forming an elastomeric membrane of an adjustable implant according to an aspect of the disclosure;

FIG. 25 is a cross-sectional view of a portion of an elastomeric membrane formed from the mandrel of FIG. 24, during a subsequent processing step, according to an aspect of the disclosure;

FIG. 26 is a cross-sectional view of a portion of the elastomeric membrane of FIG. 25, during a subsequent processing step according to an aspect of the disclosure;

FIG. 27 is an adjustable implant formed from the elastomeric membrane of FIG. 26 according to an aspect of the disclosure;

FIGS. 32A-32E are schematic drawings illustrating an exemplary process for forming the implant of FIG. 31 according to an aspect of the present disclosure;

DESCRIPTION OF THE INVENTION

Figure 1:
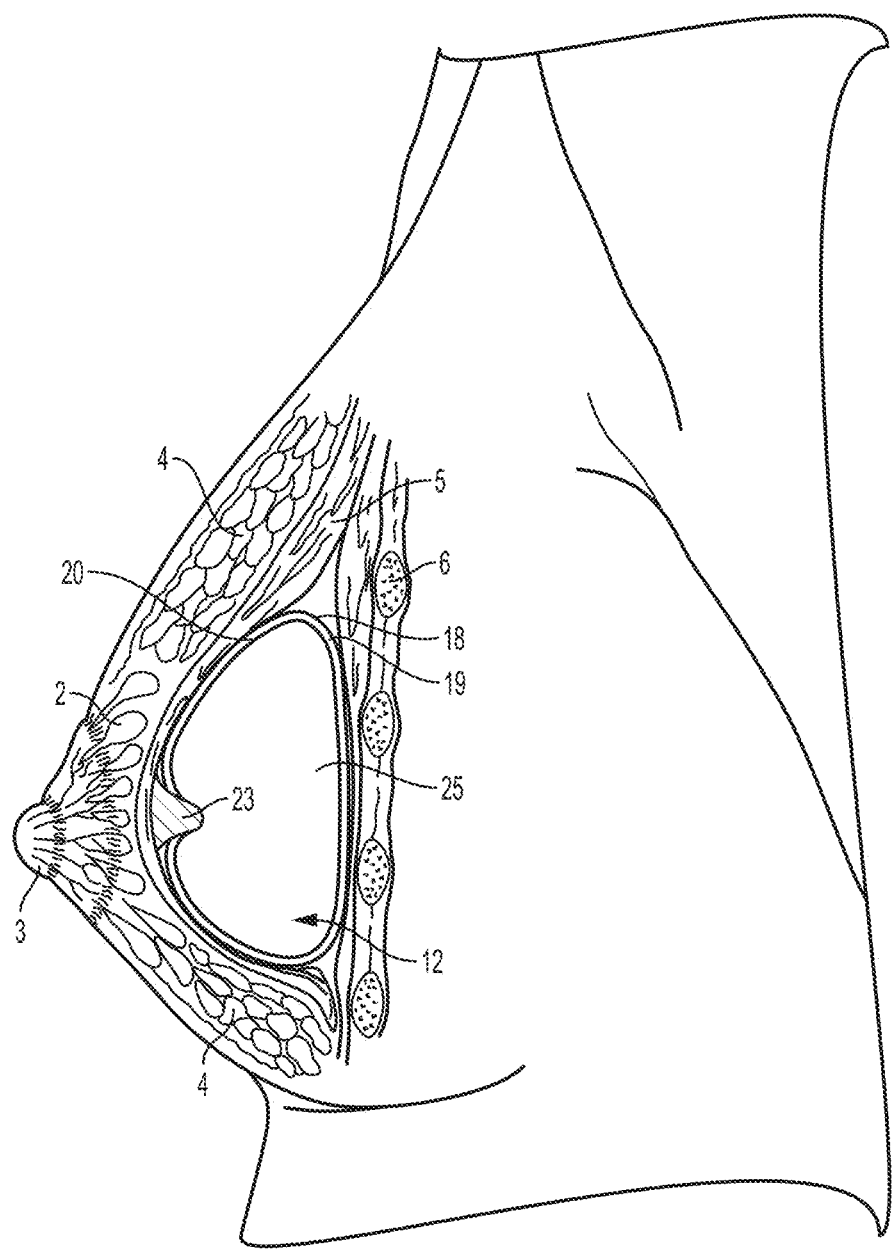
FIG. 1 is a sagittal view of a female human body through the left breast showing anatomical detail along with in situ placement of an adjustable implant according to an aspect of the disclosure.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all subranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

With reference to the Figures, in general, the present disclosure is directed to an implant 12, 112, 210 including an elastomeric membrane enclosing or partially enclosing a cavity or interior volume. The membrane can be pre-stressed prior to filling. For example, pre-stressing can include expanding the volume of the cavity substantially beyond both the volume of the membrane when cured and the volume of the finished implant. In some examples, a 500 cc membrane can be expanded to 15 liters (e.g., an expansion of 3000%). Pre-stressing modifies stretching and resiliency of the membrane, which is desirable in some applications. Following pre-stressing, the cavity can be filled with a fluid, such as a biocompatible water-soluble gel, a silicone gel, or saline solution. The membrane is desirably under significant contraction or compression. However, forces contracting the membrane should be balanced with other forces on the membrane to produce a stable implant 12, 112, 210. By nature of its design, the elastomeric membrane produces a different feel than other exemplary implant membranes. In some examples, at least a portion of the membrane can entirely enclose the cavity. In other examples, the membrane can define an opening or hole filled by a plug (e.g., a cured elastomeric material), thereby enclosing the cavity.

The implant 12, 112, 210 of the present disclosure can be used for various breast reconstruction and augmentation procedures, but is not limited to these procedures. For purposes of illustration and description, breast implants will be utilized as exemplary of procedures in which the disclosed implant can be used. Variations of the invention can be utilized for tissue volume replacement and as a tissue expanding device to form tissues in post-traumatic surgery or in advance of planned surgery to prepare tissue flaps. As such, these implants 12, 112, 210 can be employed as a permanent prosthesis or a temporary device, as indicated. The methods of manufacture disclosed herein can be used to produce implants with custom forms and/or material properties for specific patients or procedures at an accessible cost. As such, the implants 12, 112, 210 disclosed herein can be employed in planned, highly invasive surgeries, such as large tumor removal. For example, an implant can be fabricated in advance to replace the desired volume and form of tissues removed. As such, the implant can be utilized to be slowly expanded or contracted over time to achieve the desired shape allowing tissues to slowly conform in a safe and predictable manner In some preferred and non-limiting embodiments or aspects, one or more layers or zones 18, 20, 118, 120 of the elastomeric membrane are continuous or substantially continuous and, preferably self-sealing. Including continuous elastomeric layers or zones enhances structural integrity of the implant shell, such that the implant can be filled to higher pressures and/or expanded substantially beyond a natural volume without risk of rupture. Thus, in a preferred and non-limiting embodiment or aspect, the continuous and self-sealing nature of the membrane allows for adjustability (e.g., adjusting implant volume by filling or removing fluid) without the need of special ports and filling valves.

In further preferred and non-limiting embodiments or aspects, an outer surface of the elastomeric membrane is textured, for example, to improve adhesion and/or interaction with breast tissue. For example, channels, ridges, or other features of a textured surface may be selected or provided for permitting or enhancing ingrowth or adhesion of breast tissue to the exterior surface of the implant. In some examples, textured or roughened regions of an implant 12, 112, 210 can create a fixation surface for adhering specific areas of the implant to breast tissue. In some examples, features of the texturing are imparted to the exterior surface of the implant during formation of the outer layers of the implant, for example, by casting in a mold. In particular, texture features etched or otherwise produced on an inner surface of the mold are imparted to the exterior surface of the implant. The texture can be a repeating pattern across the entire external surface of the implant. In other examples, different portions of the implant surface have different texture patterns to impart different interaction with body tissue to different areas of the membrane. For example, posterior portions of the implant 12, 112, 210 can include roughened fixation surfaces for improved adhesion to the chest wall. In other examples, anterior portions of the membrane may include a more substantial degree of texture (e.g., higher ridges and deeper grooves) to permit ingrowth of muscle tissue to the implant surface. In other examples, designs can be provided on the exterior surface of the implant to assist in placement of the implant. For example, guidelines for orientation of the implant could be molded to the implant surface.

In other preferred and non-limiting embodiments or aspects, an implant 12, 112, 210 formed from an elastomeric membrane or shell is filled with a cohesive gel 212. A cohesive gel 212 material refers to a substantially form-stable material, which maintains its shape when cured. In contrast, flowable materials, such as saline, are not form stable. The cohesive gel 212 is generally a biocompatible material, such as silicone, which can be injected or poured into an implant shell or mold in a flowable state and cured to produce a form-stable structure.

In some preferred and non-limiting embodiments or aspects, the cohesive gel 212 is enclosed within an elastomeric shell formed from a plurality of silicone layers. The elastomeric membrane or shell can be under contraction such that the elastomeric shell exerts a contracting force on inner portions of the implant, including the cohesive gel. For example, outer layers of the shell can be cured to enclose a smaller volume than the volume enclosed by the finished implant. In that case, outer layers of the shell exert a contraction force on inner layers of the shell and on the cured cohesive gel material. The contraction force of the outer layers is balanced against outwardly directed forces of the inner layers and/or cohesive gel. The balance of contracting and outwardly extending forces contributes to mechanical properties and feel of the implant. For example, inner layers of the membrane and/or the cohesive gel material may press against the outer layers, thereby providing a level of resiliency and softness, which gives the implant a more natural feel. Previously, manufactures attempted to improve the softness and feel of implants by making the shell as thin as possible so that the feel of the cohesive gel portion of the implant would be more noticeable than the feel of the shell. In order to make the shell as thin as possible, tougher silicone materials were used for the shell. However, conventional implants formed from thin, tough silicone shells are susceptible to rippling. In the presently disclosed implant, the membrane is contracted against the cohesive gel, which reduces occurrence of rippling. In addition, the balance of forces produced between the cohesive gel and contracting shell means that a thicker shell can be used while still obtaining desirable softness and natural feel. Use of a thicker membrane or shell further reduces effects of rippling.

Exemplary Implant

Figure 2:
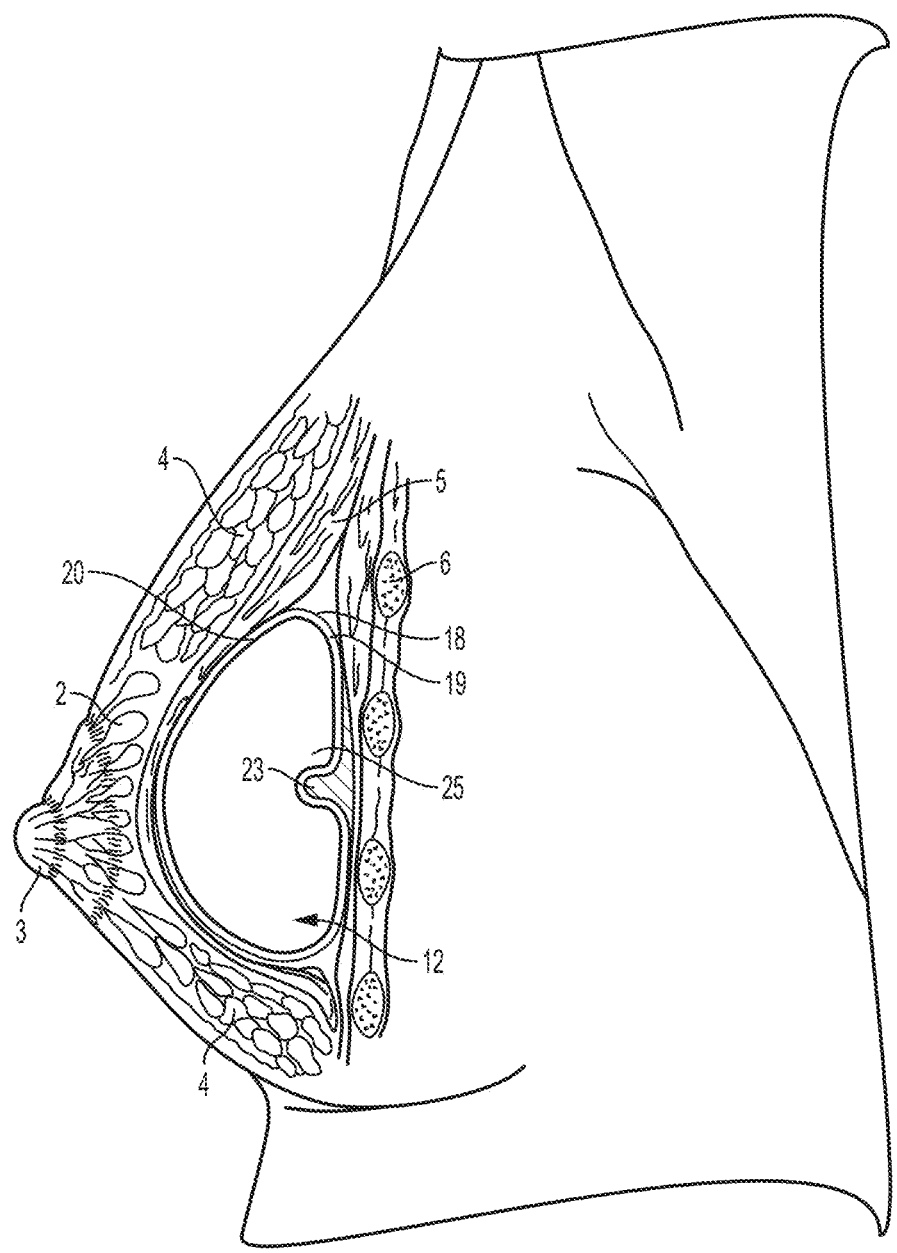
FIG. 2 is a cross-sectional view of the adjustable implant of FIG. 1 inserted in a patient's breast in a reverse orientation.

With reference to FIG. 1, a cross-sectional view of an implant 12 placed within the left female human breast is illustrated. The implant 12, according to a preferred and non-limiting embodiment, is in a sub-muscular anatomical position under a pectoralis chest muscle 5. Alternatively, the implant 12 can be positioned sub-muscularly or in subglandular placement. There are variations on these placements, but these two categories of placement are the most common practice. The sectional view of FIG. 1 provides basic anatomical landmarks for clarity. The implant 12 is posteriorly positioned against the chest wall tissues and underlying ribs 6. Anteriorly, the implant 12 may be positioned under the chest muscle tissue 5 with the greatest muscular coverage enveloping the superior anterior aspects of the implant 12. Anterior to the muscle tissues 5 are an intact subcutaneous fat 4 and mammary glands 2. A nipple 3 is the most anterior structure to the implant 12. As shown in FIG. 1, the implant 12 can be oriented such that a plug 23 that seals the inner cavity of the implant is positioned adjacent to the nipple 3. In other examples, as shown in FIG. 2, the implant can be positioned with the plug adjacent to the chest wall and underlying ribs 6.

Elastomeric Membrane

With reference to FIGS. 1-4, according to a non-limiting aspect or embodiment, the implant 12 generally includes an elastomeric membrane, also referred to as a shell, formed from multiple laminated elastomeric layers. In some preferred and non-limiting aspects and examples, the membrane or shell is between about 0.75 mm to 5.0 mm thick, preferably between about 1.0 mm and 3.0 mm thick, and more preferably, about between 1.8 mm and 2.5 mm thick. However, shells having a thickness of greater than 5.0 mm may be used for particular applications. In some examples, the thickness of the membrane can vary around the circumference of the implant 12. For example, portions of the membrane intended to be positioned near an opening 24 and/or plug 23 may be made thicker than other portions of the membrane. In other examples, portions of the membrane intended to be positioned near harder anatomical structures may be made to be thicker to reduce the possibility of leakage and/or to improve implant safety.

Figure 3:
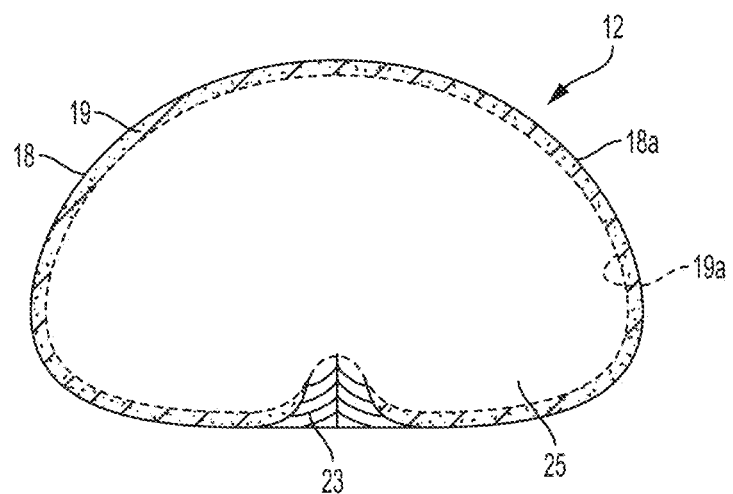
FIG. 3 is a cross-sectional view of another embodiment of an adjustable implant according to an aspect of the disclosure.
Figure 4:
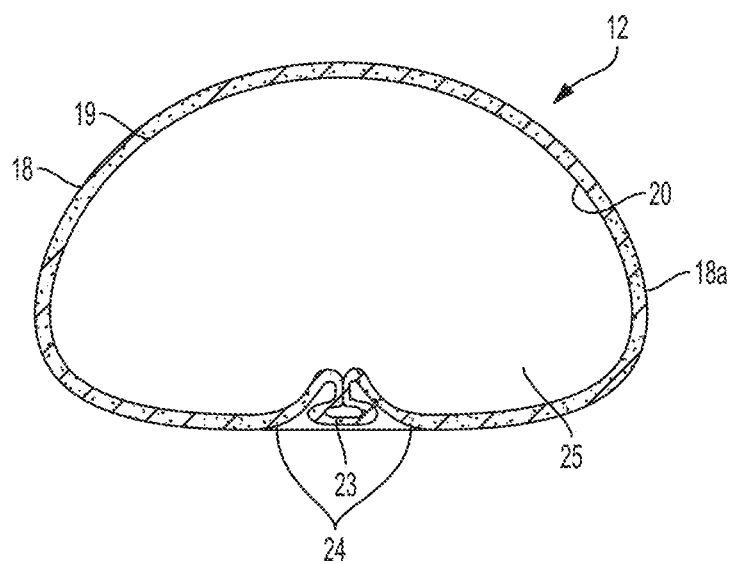
FIG. 4 is a cross-sectional view of another embodiment of an adjustable implant according to an aspect of the disclosure.

Generally, the membrane includes at least several high-performance silicone elastomer layers for enhanced shell integrity. Variable elastomers are utilized to provide a membrane with self-sealing properties. Although the membrane may include numerous layers, the layers may be generally classified in two or more zones or regions having similar material properties and/or degrees of contraction, namely, an outer zone 18 and an expanded or middle zone 19. In the case of a two-zone implant 12, only the outer zone 18 and the expanded or middle zone 19 are provided. As shown in FIGS. 1, 2, and 4, a three-zone implant 12 can include the outer zone 18, the expanded or middle zone 19, and an inner zone 20. A two-zone implant 12 is shown in FIG. 3.

In some non-limiting embodiments or aspects, the multiple layers of the elastomeric membrane are classified into the zones based on the volume enclosed by the respective layers at the time of curing. For example, as discussed in greater detail herein, the volume enclosed by the layers of the outer zone 18 at the time of curing may be smaller than the volume enclosed by the layers of the expanded or middle zone 19 at the time of curing the middle zone 19 layers, thereby causing the layers of the outer zone 18 to exert a contracting force against the layers of the middle zone 19. For example, a volume enclosed by the outer zone 18 at the time of curing may be expanded by between about 10% and about 500% or more before forming the expanded or middle zone 19. In some embodiments, the degree of expansion of the outer zone 18 is selected so that the completed implant 12 naturally returns to a size which is slightly larger than the size of the outer zone 18 when originally formed. For example, the completed membrane 214 may naturally conform to enclose an interior volume which is between about 10% and about 40% larger than the volume enclosed by the outer zone 18 at the time of forming the outer zone 18.

In order to impart such a contracting force, at least some of the layers of the outer zone 18 must be durable, essentially impermeable, should exhibit stable memory characteristics, and still remain very elastic. For example, the outer zone 18 layers can have a Shore hardness of about Shore A-10 to A-40, and preferably about Shore A-20 to Shore A-30. In some examples, layers of the respective zones 18, 20 can be formed at different enclosed volumes. For example, the cured outer zone 18 could be expanded incrementally and, during each expansion, a few layers of the middle zone 19 could be formed. In this way, the layers of the expanded or middle zone 19 may be subjected to varying contracting forces based, in part, on the volume enclosed by each respective middle zone 19 layer when formed and/or cured. However, in any case, it is desirable that in the completed implant 12, expansion and contracting forces provided by the membrane layers are balanced resulting in a stable implant. The balance of expansion and contracting forces give the completed implant shell desirable properties including, for example, rebound and natural feel.

In some preferred and non-limiting embodiments or aspects, an exterior surface of an outermost layer of the outer zone 18 includes one or more textured portions. For example, textured portions can include a pattern of ridges and protrusions for improving implant adhesion. In some embodiments or aspects, the pattern can resemble granulated or crystalline structures on the implant surface. In other preferred and non-limiting embodiments or aspects, an exterior surface of an outermost layer of the outer zone 18 includes a cross-hatch design pattern formed from interconnecting lines or waves extending across at least a portion of the implant surface. In other embodiments or aspects, the textured pattern can include a plurality of protrusions extending from the exterior surface 18a of the implant 12. For example, such protrusions can be evenly spaced or positioned across a portion of the exterior surface.

Figure 5A:
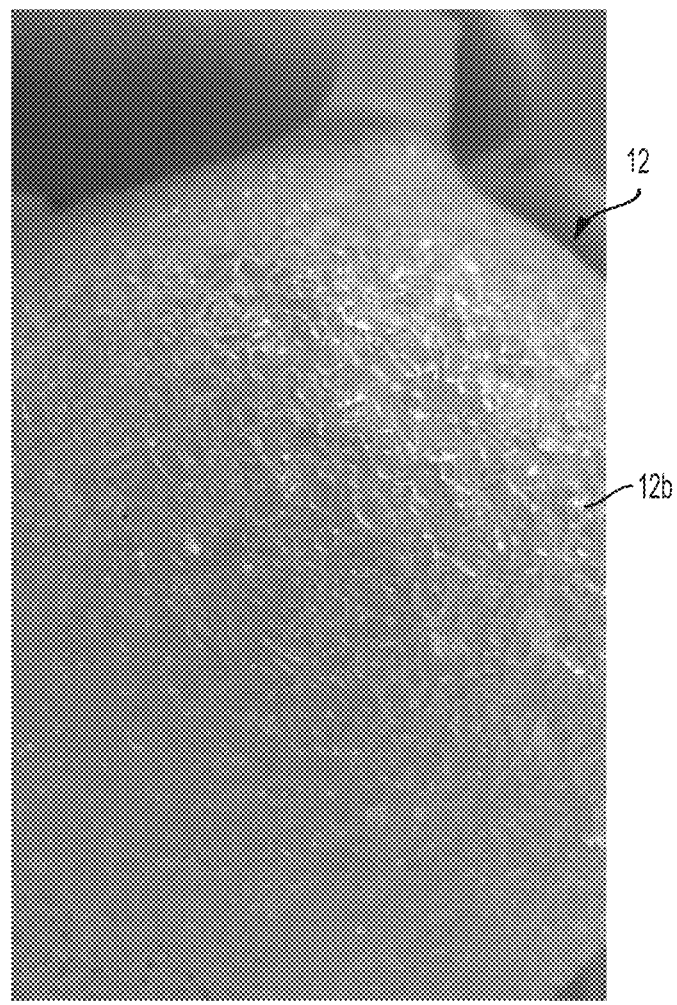
FIGS. 5A to 5C are photographs of textured portions of an exterior surface of an implant according to aspects of the disclosure.
Figure 5B:
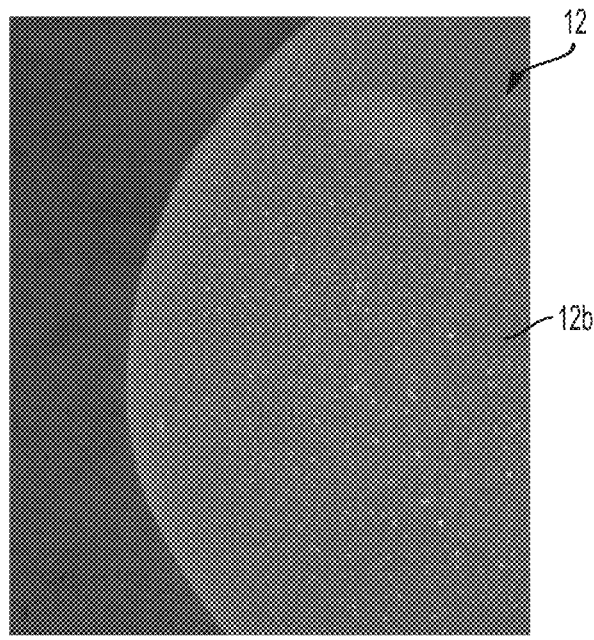
Figure 5C:
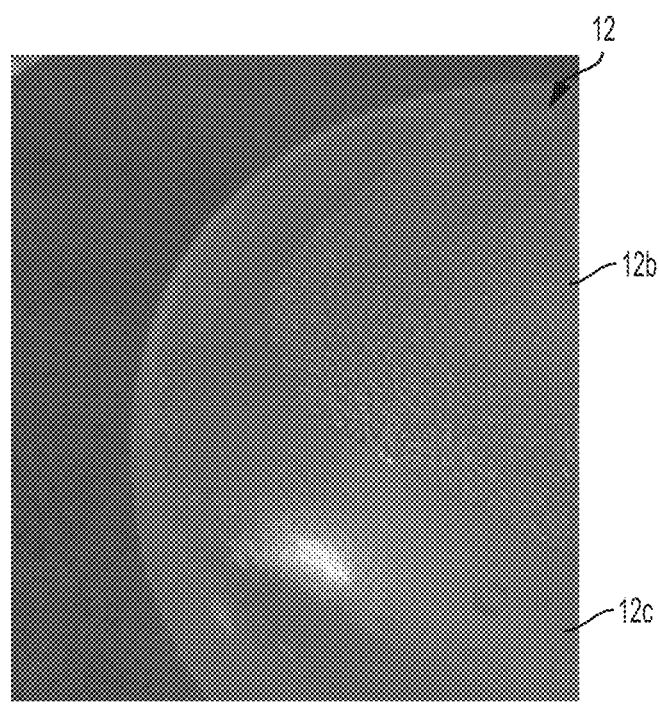

Photographic images showing exemplary textured portions of an implant 12 are shown in FIGS. 5A-5C. For example, a portion of an implant 12 including a textured portion 12b having a molded granulated or crystalline structure is shown in FIGS. 5A and 5B. An implant 12 having a textured portion 12b having a molded granulated or crystalline structure and surrounded by a flat portion or surface 12c is shown in FIG. 5C.

With reference again to FIGS. 1-4, in some preferred and non-limiting embodiments or aspects, the expanded or middle zone 19 includes multiple layers of softer elastomeric material applied and/or laminated to the outer zone 18 layers. The layers of the middle zone 19 can be formed by blending silicone materials with different hardness to obtain desired properties. Desirably, the change in composition of the layers occurs gradually so that a transition between adjacent layers is not too abrupt. Adjacent layers with similar properties adhere together better than layers with different properties. For example, layers of the expanded or middle zone 19 near the outer and inner zones 18, 20 may be formed to have a similar hardness to the outer and inner zones 18, 20. Moving toward the middle of the middle zone 19, the layers can be made to be gradually softer by increasing the portion of soft silicone material in the silicone blend. The total thickness of the middle zone 19 may be greater than the outer zone 18. Some or all of the middle zone 19 layers may have a tacky, but cured state, which remains soft and elastic. For example, soft, tacky layers of the expanded or middle zone 19 can have a durometer of about Shore 00-10 to Shore 00-40. Such pliable characteristics allow these layers to be put in a state of compression. Specifically, as discussed in detail herein, during formation of the elastomeric membrane, the cured outer zone 18 is expanded to allow for the larger volumetric form to be established. Once the middle zone 19 is cured over the expanded outer zone 18, the outer zone 18 and the middle zone 19 are retracted to a volume and shape that more closely resembles its original cured shape. However, the cured outer zone 18 generally is not retracted all the way to its original state. Nevertheless, the outer zone 18 still provides substantial contraction on the softer middle zone 19 by causing the middle zone 19 layers to conform to a lesser volume.

In some preferred and non-limiting embodiments or aspects, the outer zone 18 and/or the expanded or middle zone 19 can include a combination of soft and hard layers. For example, soft and hard layers can be laminated one on top of the other in alternating fashion, thereby providing a zone 19, 20 including both soft and hard properties.

For an elastomeric membrane having only two zones, as shown, for example, in FIG. 3, at least an innermost layer 19a of the middle zone 19 should be harder than the other layers of the middle zone 19, thereby enclosing and providing a contracting force for the soft tacky layers of the middle zone 19. However, unlike for a three-zone membrane in which the inner zone 20 is cured after the membrane 12 is retracted, the innermost layer 19a of the middle zone 19 is formed while the membrane is in an expanded state. For example, the harder innermost layer 19a may be formed on the inner surface of the middle zone 19 just before the membrane is retracted. The innermost layer 19a may have a composition similar to the harder and more rigid layers of the outer zone 18.

In some preferred and non-limiting embodiments or aspects, the membrane can define an opening 24 for permitting access to the interior of the implant 12 during formation and filling. For example, a plug 23 can be inserted and cured in the opening 24 to seal the interior volume of the implant. In some examples, the plug 23 functions as a self-sealing injection port that can be utilized to pre-fill the implant 12 enclosed by the membrane to a desired volume prior to implantation. This plug 23 may take a variety of forms and configurations, such as a one-way valve, a flapper valve, an elastic valve, and the like. Further, the plug 23 may include one or more apertures or conduits through which to insert specified fluids into various areas of the implant 12.

In other preferred and non-limiting embodiments or aspects, the plug 23 is formed by folding a small portion of the elastomeric layers of the membrane over the opening 24 to seal the opening 24. For example, as shown in FIGS.

16-18, the formed membrane can include a neck portion extending from the opening 24 which must be removed to form the completed implant. The neck portion is often cut off after the elastomeric membrane is cured. In some examples, portions of the neck portion can be folded into the opening 24 to form the plug 23 rather than being cut off from the implant. In other embodiments or aspects, the plug 23 is a flat patch or piece of elastomeric material which is mounted to the implant 12 over the opening 24 using, for example, adhesive or flowable elastomeric material. The flowable elastomeric material can be cured to secure the patch to the elastomeric membrane. In other embodiments or aspects, the plug 23 can be formed by pouring a small amount of flowable silicone in the opening 24. The flowable material can be cured to form a suitable seal for the implant.

After the layers of the membrane are cured, in some preferred and non-limiting embodiments or aspects, the chamber or interior volume of the implant 12 can be filled with biocompatible fillers, such as saline or saline with biocompatible thickening agents, so that in the event of leaking, the saline is naturally absorbed. Thickening agents can be designed to provide additional sealing ability from within the implant. Methylcellulose has a high molecular mass and can be added to the saline to give it gel-like properties. Aqueous carboxy-methylcellulose has proven biocompatibility and is utilized in some cosmetic filling agents. Polyethylene glycol (PEG) and saline would also be a suitable combination with thickening characteristics. The high molecular mass of PEG and other similar thickening agents will reduce the risk of leakage from the membrane. Previously, membranes of breast implants were generally made as thin as possible to achieve a softer feel. However, thinner membranes impose greater risks with respect to puncture, capsular contraction, and gel or fluid bleeds. The membranes described herein are generally thicker than currently available membranes resulting in a safer design. For example, the membrane is preferably about 1.8 mm to 3.0 mm thick, and can be as thick as 5.0 mm. The contraction properties of the present implant 12 are selected to provide the desirable natural, soft feel even when a thicker membrane is used.

Exemplary Three-Zone Implant

With reference to FIG. 4, an implant 12 comprising a three-zone shell is illustrated. An implant 12 having a membrane formed in a three-zone configuration facilitates the self-sealing capability of the implant 12. The implant 12 is generally similar in size and shape to the other exemplary implants described herein. For example, the implant 12 generally includes a continuous or substantially continuous elastomeric membrane that has a total thickness of about 0.75 mm to 5.0 mm, preferably about 1.0 mm to 3.0 mm, and more preferably about 1.8 mm to 2.5 mm thick. The membrane encloses a volume or chamber of about 80 cc to 800 cc. The membrane includes the outer zone 18 formed from a harder silicone material of about Shore A-10 to Shore A-40, and preferably from about Shore A-20 to Shore A-30. The elastomeric layers of the outer zone 18 enclose and apply substantial compression to soft, tacky, but cured layers of the middle zone 19. As discussed in connection with other exemplary implants, the layers of the middle zone can have a durometer of about Shore 00-10 to Shore 00-40.

The membrane further comprises an inner zone 20 formed from one or more elastomeric layers that are strong and highly resistant to permeability. The layers of the inner zone 20 remain elastomeric and have significant ability to stretch and return to their original shape. These inner zone 20 layers are cured and set to a desired volume and shape, which encapsulates the interior volume or chamber of the implant 12. As described herein, the layers of the inner zone 20 are formed when the membrane is in a retracted state. Accordingly, the layers of the inner zone 20 exert a contracting force to the layers of the middle zone 20 contributing to the substantial compression on the middle zone 20. Accordingly, the inner zone 20 contributes to the desirable properties of the implant 12 by enhancing compression on the middle zone 19.

In a three-zone implant, the middle zone 19 includes multiple layers of softer elastomeric material to envelop the inner zone 18 layers in a significantly expanded state. The middle zone 19 may be thicker than the inner zone 18 or the outer zone 20. During formation of the membrane, the inner zone 18 is expanded to allow for the larger volumetric form to be established. Once the middle zone 19 is cured, the inner zone 18 and the middle zone 19 are retracted to a volume and shape representative of the inner zone 18 in its original cured shape. Thus, the softer middle zone 19 is in significant contraction as it is forced to conform to a lesser volume. The outer zone 20 layers are then formed to envelope the middle zone 19 layers. The outer zone 20 has similar or identical properties to the inner zone 18 layers, being elastomeric, yet strong and resistant.

The resultant membrane includes a middle zone 19 that is thicker and formed from softer elastomeric membrane, under contraction. The middle zone 19 is sandwiched between the inner zone 18 and the outer zone 20 of stronger and more stable elastomeric compounds. In some embodiments or aspects, the membrane may be different thicknesses at different areas of the implant 12. Further, as discussed above, the harness of the layers of the middle zone 19 can vary gradually such that adjacent layers of the membrane have similar mechanical properties.

The three-zone configuration can facilitate the self-sealing capability of the membrane. However, the design and configuration of the membrane is not limited to the three-zone configuration. Other arrangements of elastomeric layers may also be employed to provide the self-sealing ability of the membrane. Furthermore, as will be appreciated by one having ordinary skill in the art, manipulation of these zone layers and their configuration will produce further advantages of this invention. For example, multiple layers under contraction will increase the integrity and self-sealing potential of the membrane. Thickness of the layers under contraction also relates directly to integrity of the membrane. Therefore, a balance between the optimal number of layers and layer thickness should be established for particular applications.

In some preferred and non-limiting embodiments or aspects, the implant 12 formed from a three-zone membrane can be punctured with a non-coring needle to access one or more chambers enclosed by the membrane. Non-coring needles are used to puncture the membrane without removing any of the silicone material forming the membrane layers. The geometry of a non-coring needle spreads and expands the silicon at the entry site. Upon retraction of the needle from the membrane, the silicone self-seals at the penetration site. The silicone must be under contractive forces to self-seal. This contraction is achieved by retaining the silicone membrane under mechanical compression from other elastomeric layers.

The self-sealing properties of the membrane produces an implant shell exhibiting properties different from existing implants. The compression of the middle zone 19 changes how the inflation forces are manifested in terms of the general feel of the implant 12. More specifically, the implant 12 can be varied in design to produce a more natural feel with less of an inflated or balloon characteristic. Furthermore, the properties of the membrane introduce a favorable variable that can be incorporated in various single or multiple chamber designs. For example, it is possible to alter the characteristics of the membrane to produce a saline-filled implant with more silicon-like characteristics.

Method of Forming the Implant

Having generally discussed the structure of different embodiments of an elastomeric membrane and implant, methods of manufacture of such implants will now be described in detail. As will be appreciated by one of ordinary skill in the art, the manufacturing possibilities for such implants are extensive with respect to methods and materials.

Reverse Casting Method

In some preferred and non-limiting embodiments or aspects, the membrane is formed in a mold in reverse order (e.g., a reverse casting method) from an exterior layer to an innermost layer. The methods disclosed herein also include varying a volume enclosed by the respective layers, thereby imparting a substantial contracting force, particularly to the middle layer 19 of the implant 12.

Figure 6:
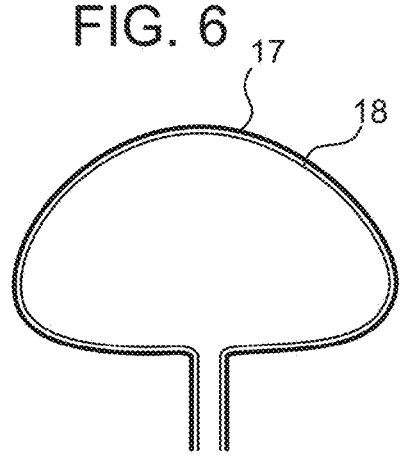
FIG. 6 is a cross-sectional view of a casting mold for forming an elastomeric membrane according to an aspect of the disclosure.

With reference to FIGS. 6-11, a method of forming the implant 12 by casting into a mold is illustrated. Various methods of casting may be employed from simple manual techniques to mechanical spin casting. The layers of the respective zones 18, 19, 20 are cast and cured in the reverse order, starting with the layers of the outer zone 18. As shown in FIG. 6, a mold 17 is utilized to produce the viscoelastic layers of the outer zone 18, which are, desirably, very durable, essentially impermeable, exhibit stable memory characteristics, and still remain very elastic. In some preferred and non-limiting embodiments or aspects, the mold 17 is formed from a clear material to permit visual inspection during the casting process. The mold 17 may be a flexible structure that can be expanded and contracted to form layers and/or zones having different enclosed volumes. For example, the mold 17 can be formed from various flexible and stretchable plastics. In other embodiments or aspects, the mold 17 can be formed from a rigid, non-expandable material, such as glass, having a constant volume and used solely for forming the layers of the outer zone 18. In that case, other zones (e.g., the middle zone 19 and/or the inner zone 20) can be formed once the cured layers of the outer zone 18 are removed from the mold 17. For example, as discussed herein, the cured outer zone 18 can be inserted into an expandable bladder 17a during formation of the middle and/or inner zones 19, 20. In other examples, the cured outer zone 18 may be sufficiently rigid that the middle and/or inner zones 19, 20 can be formed in the cured outer zone 18 without using a mold or bladder to support the cured outer zone 18.

In some examples, the mold 17 can be disposable and configured to be used one time. For example, molds formed from plastics can be inexpensive to manufacture and can be discarded after a single use. Advantageously, implants formed from a disposable mold can be highly customized for particular uses. For example, implant volume and shape can be customized for particular patients. In addition, texturing on the inner surface of the mold can be specifically adapted for particular uses.

Figure 7:
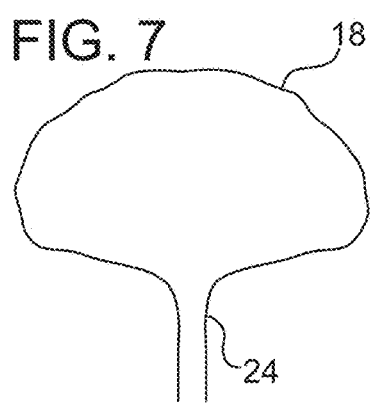
FIG. 7 is a cross-sectional view of a portion of an elastomeric membrane formed from the mold of FIG. 6.
Figure 10:
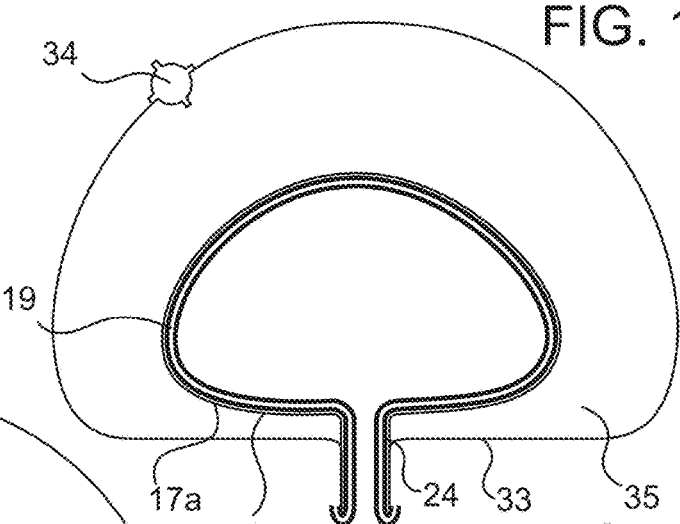
FIG. 10 is another cross-sectional view of the apparatus of FIG. 8 illustrating a processing step for forming an elastomeric membrane from the portion of the membrane of FIG. 7.

As shown in FIG. 6, a flowable material, such as liquid silicone, is introduced to an interior of the mold 17. The flowable material can be dispersed across the inner surface of the mold 17 by spinning and/or inverting the mold 17 until the entire surface is covered. The flowable material desirably flows into the texturing, ridges, and channels on the inner surface of the mold 12, such that the exterior surface of the outer zone 18 conforms to the texturing of the inner surface of the mold 17. Once the flowable material is evenly dispersed, it can be allowed to stabilize and cure. In some examples, the flowable material cures at room temperature. In other examples, the mold 17 and flowable material contained therein can be heated to cure the flowable material, thereby forming an elastomeric layer. Additional layers of the outer zone 18 can be laminated to the inner surface of the outermost layer 18a, thereby forming a thicker outer zone 18. The outer zone 18 can be complete once the collected layers reach a desired thickness. The purpose of this initial stage is to produce a complete form of the viscoelastic layers of the outer zone 18 as seen in FIG. 6. An illustration of a cured outer zone 18 removed from the mold 17 is shown in FIG. 7.

Figure 8:
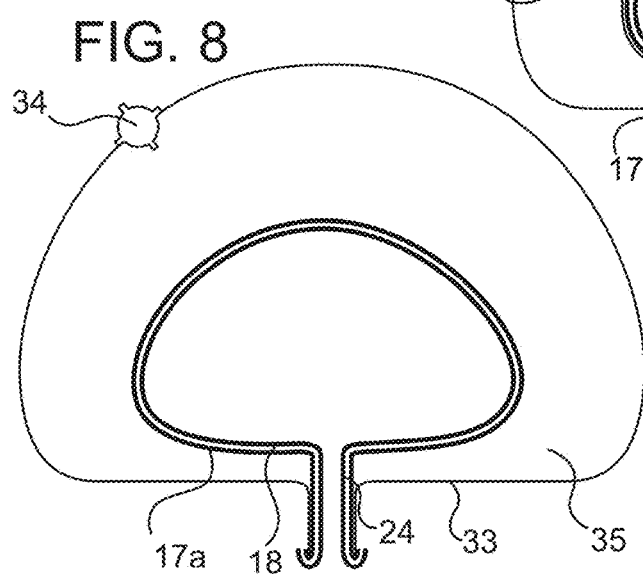
FIG. 8 is a cross-sectional view of an apparatus for secondary casting for forming additional elastomeric layers on the portion of the elastomeric membrane of FIG. 7.
Figure 11:
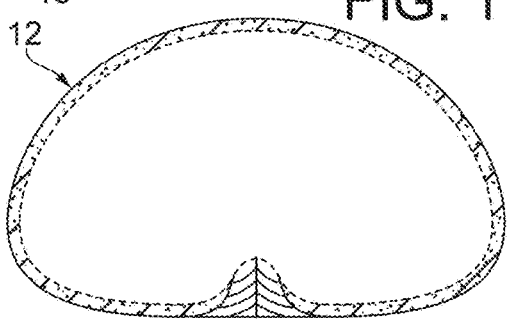
FIG. 11 is a cross-sectional view of an adjustable implant formed from the elastomeric membrane of FIG. 10.

As shown in FIG. 8, an apparatus 33, such as a vacuum evacuation chamber, is used to expand and retract the cured outer zone 18 and/or mold 17 to cast the remaining layers. The outer body of the apparatus 33 is rigid with an evacuation valve 34 and an internal bladder 17a. The purpose of this apparatus 33 is to expand and retract the outer zone 18 layers and/or mold 17 through the remainder of the laminating process. The bladder 17a has a base shape reflective of the final form of the preferred and non-limiting embodiment of the implant illustrated, for example, in FIGS. 1-4. The bladder 17a has elastic properties and strong memory of form. In some examples, the bladder 17a may include perforations to allow communication between the mold cavity and evacuation chamber 35 created by the outer body of the apparatus 33.

With continued reference to FIG. 8, the previously formed outer zone 18 viscoelastic layers are positioned within the bladder 17a. In some examples, the outer zone 18 layers can remain in the mold 17, and both the zone 18 and mold 17 can be inserted in the bladder 17a. In other examples, the outer zone 18 layers can be removed from the mold 17 and inserted in the bladder 17a. The cured outer zone 18 can be inserted directly in the evacuation chamber 35 without a supporting mold 17 or bladder 17a. Once inserted in the chamber 35, the bladder 17a can be retracted to conform to the shape of the cured outer zone 18. A slight vacuum pressure may be required to hold the outer zone 18 layers and/or mold 17 in place. The bladder 17a and outer zone 18 layers are sealed around a collar of the apparatus 33 body. The vacuum pressure is maintained by utilizing an evacuating valve 34. In certain embodiments, the contact surface between the bladder 17c and the viscoelastic layers of the outer zone 18 may require lubrication to equalize and marry the conforming shapes. Once positioned and retained, the apparatus 33 is configured to expand the bladder 17a along with the outer zone 18 viscoelastic layers to a desired size and shape.

Figure 9:
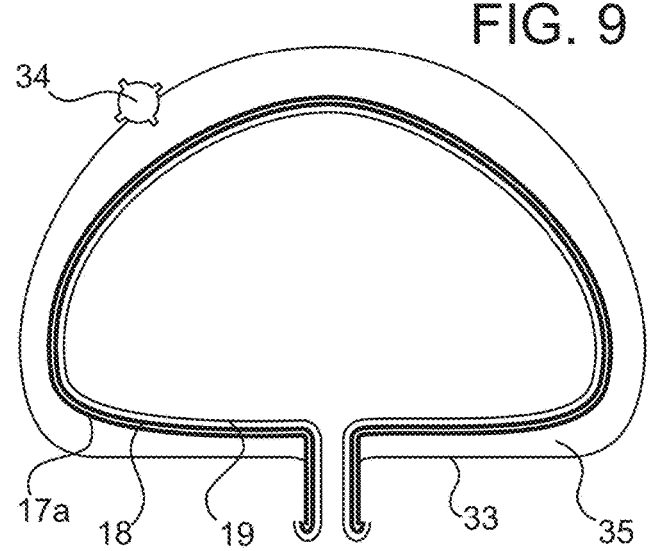
FIG. 9 is a cross-sectional view of the apparatus of FIG. 8 illustrating a processing step for forming an elastomeric membrane from the portion of the membrane of FIG. 7.

As shown in FIG. 9, the complex of the bladder 17a and the previously formed outer zone 18 layers are expanded and retained in an expanded form by closing the evacuation valve 34 to seal the evacuation chamber 35. For example, if the layers of the outer zone 18 have a cured diameter of 7 cm and an enclosed volume of 180 cm$^3$, in the expanded form, the outer zone 18 can have a diameter of about 15 cm and an enclosed volume of about 1770 cm$^3$. Once expanded the desired amount, the expanded mold cavity is ready to laminate the middle zone 19 layers. In some examples, as discussed herein, one or more of the middle zone 19 layers are required to attain a tacky, but cured state, which remains soft and elastic. In particular, these middle zone 19 layers desirably have pliable characteristics that allow the layers to be placed in a state of compression. The middle zone 19 layers are cast in one or more layers by manual or mechanical processes, similar to the previously cast outer zone 18 layers.

In some preferred and non-limiting embodiments or aspects, the implant 12 can be formed as a two-zone implant including only elastomeric layers of the outer zone 18 and the middle zone 19. In that case, at least the innermost layer 19a of the middle zone 19 is a harder layer similar to the layers of the outer zone 18. In order to deposit the hard innermost layer 19a of the middle zone 19, after forming the soft and tacky layers of the middle zone 19 in the manner described above, the innermost layer 19a is formed by introducing a harder elastomeric material to the interior cavity of the mold 17, dispersing the elastomeric material over the surface of the membrane, and curing the material to form the hard innermost layer 19a.

After casting of the middle zone 19 layers is complete, the layers are subjected to compression by opening the evacuation valve 34 to place the cured outer zone 18 and middle zone 19 in a retracted state. The process of retraction may be done in a cured or partially cured state to allow manipulation of desired characteristics of the membrane complex. This allows the bladder 17a to return to its original memory shape with the laminated outer zone 18 layers and middle zone 19 layers. It is noted that although the bladder 17a may return to its original shape, the layers of the outer zone 18 generally do not retract all the way to their original cured shape and position but, instead, assume a slightly expanded configuration compared to the original cured state. For example, for a shell in which the outer zone 18 has a cured diameter of about 7 cm and an enclosed volume when cured of about 180 cm$^3$, the final or retracted diameter of the outer zone 18 can be about 9 cm and have an enclosed volume of about 382 cm$^3$. Accordingly, the textured exterior surface of the outer zone 18, formed from contact between the outer zone 18 and the inner surface of the mold 17, is not an identical representation of the texturing and/or ridges and channels on the inner surface of the mold 17. Instead, the texturing on the exterior surface of the implant 12 assumes a slightly expanded configuration. The texturing on the inner surface of the mold 17 can be selected with the degree of expansion of the formed implant 12 in mind.

The formed elastomeric membrane can be removed from the mold 17 and pre-stressed prior to filling to modify the resiliency and elasticity of the implant. In some embodiments or aspects, pre-stressing includes stretching the membrane by expanding the volume enclosed by the membrane by a substantial amount. Some implants 12 formed by the processes described herein can be expanded by up to 3000% without rupture (e.g., a 500 cc implant was expanded to 15 L). In other examples, pre-stressing the membrane can include stretching portions of the membrane to increase flexibility of selected portions of the implant. Further, in some instances, pre-stressing can include performing multiple inflations and/or adjusting a duration of each inflation or ambient temperature during inflation of the membrane. In other examples, the amount of stretching or percentage of inflation can be adjusted. In some embodiments or aspects, especially for thicker elastomeric membranes, the membrane may be warmed or heated prior to stretching or stressing. In one example, external pressure (e.g., squeezing) can be applied to portions of the membrane as it is being inflated to impart variable pre-stressing. For example, if the two poles of the implant 12 are pushed with a force towards one another, the equatorial portion of the implant 12 will expand more causing that portion of the membrane to be softer and more pliable after the pre-stressing process is complete.

Following pre-stressing, in some preferred and non-limiting aspects or embodiments, the interior volume or void of the membrane is cleaned by appropriate measures. After cleaning, the membrane can be enclosed by trimming surplus membrane formed along the apparatus 33 collar and inverting a flange remaining around the hole or opening 24 of the membrane in an inward direction toward the middle of the posterior aspect of the implant 12 to form the plug 23. The plug 23 is then cured to seal the implant 12, thereby forming a completed two-zone implant. Exemplary completed two-zone implants are illustrated, for example, in FIGS. 3 and 11.

In some preferred and non-limiting embodiments or aspects, the plug 23 is formed from viscoelastic material similar to the middle zone 19. The plug 23 functions as a self-sealing injection port that can be utilized to pre-fill the interior volume or chamber 25 of the implant to a desired volume prior to implantation. Biocompatible thickening agents can also be pre-filled prior to sealing the implant. The implant 12 is filled or partially filled with a fluid, such as saline, prior to implantation to the patient.

Figure 12:
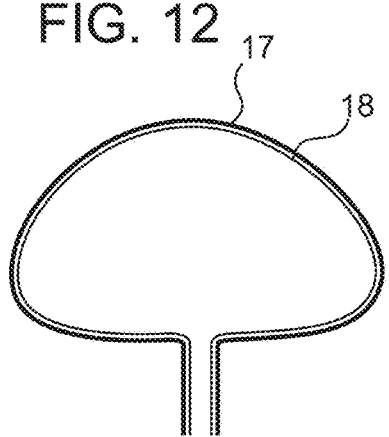
FIG. 12 is a cross-sectional view of another casting mold for forming an elastomeric membrane according to aspects of the disclosure.
Figure 13:
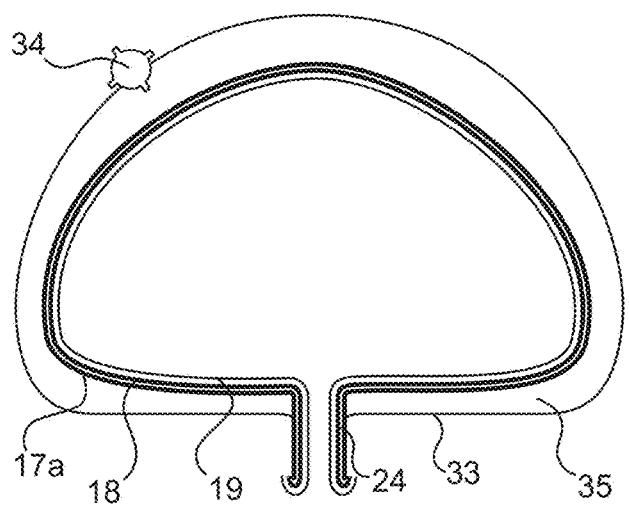
FIG. 13 is a cross-sectional view of an apparatus for secondary casting for forming additional elastomeric layers on the portion of the elastomeric membrane of FIG. 12.

With reference to FIGS. 12-15, a process for forming a three-zone implant 12 is illustrated. The process generally resembles the process for making the two-zone implant described in connection with FIGS. 6-11. In particular, as shown in FIG. 12, the elastomeric material is introduced to the mold 17 and cured to form the outer zone 18. Texturing can be transferred from the inner surface of the mold 17 to the exterior surface of the implant in the manner discussed herein. In some embodiments or aspects, after curing, the outer zone 18 is removed from the mold 17 and placed in the bladder 17a. In other examples, the mold 17 and cured outer zone 18 are inserted in the bladder 17a together. As shown in FIG. 13, the outer zone 18 and/or mold 17 are expanded and retained in an expanded form by closing the evacuation valve 34 to seal the evacuation chamber 35. As in previously described examples, the expanded mold cavity is ready to laminate the middle zone 19 layers. In some examples, one or more of the middle zone 19 layers are required to attain a tacky, but cured state, which remains soft and elastic. These middle zone 19 layers may have pliable characteristics that allow the layers to be placed in a state of compression. The middle zone 19 layers are cast in one or more layers by manual or mechanical processes, similar to the previously cast outer zone 18 layers.

Figure 14:
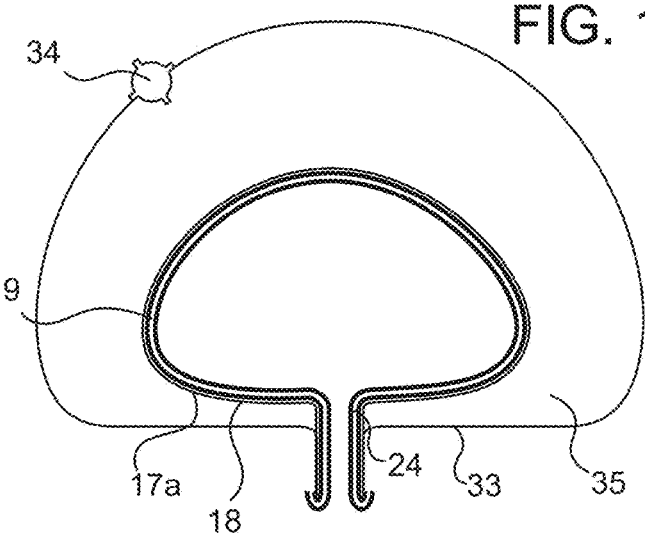
FIG. 14 is a cross-sectional view of the apparatus of FIG. 13 illustrating a processing step for forming an elastomeric membrane from the portion of the membrane of FIG. 12.

After the middle zone 19 is cured, the shell, including the outer zone 18 layers and the middle zone 19 layers, is retracted, in the manner described above. Once the zones 18, 19 are retracted, as shown in FIG. 14, the apparatus is configured for a final molding state. Specifically, the outer zone 18 and middle zone 19 are retracted to a shape representative of the final form of the implant 12. Adequate vacuum pressure remains in the evacuation chamber 35 to stabilize the form for molding. Once the membrane is stabilized in a desired form, one or more viscoelastic layers of the inner zone 20 are cast in a manner similar to the previously cast layers. For example, flowable viscoelastic material for forming layers of the inner zone 20 can be introduced to the interior surface of the membrane or shell either manually (e.g., by pouring flowable elastomeric material into the mold) or using a mechanical or automated device for introducing such flowable material. In some preferred and non-limiting embodiments or aspects, the inner zone 20 layers are very durable, essentially impermeable, exhibit stable memory characteristics, and still remain very elastic.

Figure 15:
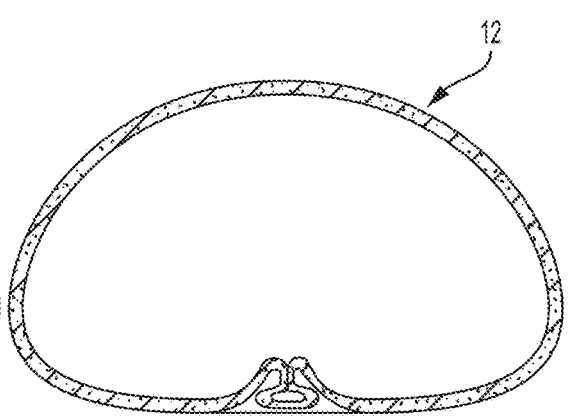
FIG. 15 is a cross-sectional view of another embodiment of an implant formed from the elastomeric membrane of FIG. 14.

In some preferred and non-limiting embodiments or aspects, the membrane can be sealed by a plug 23 in the manner described above in connection with the two-zone elastomeric membrane. In other examples, the membrane can be sealed by one or more layers of the inner zone 18, as shown in FIG. 15. For example, the layers of the outer zone 18 and the middle zone 19 may define an opening 24 for permitting casting of additional layers in the interior of the void space or chamber. The innermost layer of the inner zone 20 can be formed as a continuous layer extending into the opening 24 to seal the membrane. Once the layers of the inner zone 20 are in place, the inner zone 20 can be cured to produce the completed implant 12. Once the inner zone 20 layers are cured, the three-zone membrane is complete and ready for removal. The vacuum is released and the laminated implant shell is pulled through the collar of the apparatus 33 neck.

In some preferred and non-limiting embodiments or aspects, the implant 12 may be filled in the mold 17. For example, prior to enclosing the inner zone 20, a biocompatible gel may be introduced to the implant 12 cavity or void space. Biocompatible thickening agents can also be pre-filled prior to sealing the implant 12. The implant 12 is filled or partially filled with a fluid, such as saline, prior to implantation to a patient. Once the fluid is introduced, the cavity can be enclosed in any of the manners described herein. For example, the plug 23 can be cured in the opening 24 or a portion of the inner zone 20 can be formed to enclose the opening 24. The filled implant 12 can be removed from the mold 17 by breaking the mold 17 in half. In other examples, the mold 17 can be a reusable two-piece mold. In that case, the filled implant 12 can be removed from the mold 17 by separating the pieces of the mold 17 and removing the filled implant 12 therefrom.

In other preferred and non-limiting embodiments or aspects, the mold 17 can be formed from a degradable or dissolvable material. In that case, after the layers of the inner zone 20 are cured and/or after the completed implant 12 is filled, the mold 17 can be dissolved to release the implant 12 therefrom. In some embodiments or aspects, dissolving the mold 17 can comprise placing the mold 17 and formed implant 12 into a bath of a fluid capable of dissolving the mold 17. For example, the mold 17 may be formed from collagen. In that case, the collagen mold 17 can be dissolved by immersion in a solution of acetic acid or another suitable fluid.

In other examples, as discussed in connection with the two-zone embodiments, the formed implant 12 can be removed from the mold 17 before filling. After the implant 12 is removed, it can be filled to a desired amount for a particular patient and/or use. In that case, the unfilled implant can be removed through a small opening of the aperture and without breaking the mold. The mold can then be reused for forming additional implant devices. Other suitable steps for removing the implant from the mold, and filling the collapsed implant with a biocompatible gel or liquid, and preparing the formed implant for patient treatment will be apparent to those of ordinary skill in the art.

Drip Casting Method

In other preferred and non-limiting embodiments or aspects of a manufacturing process, drip casting can be employed to form the elastomeric membrane. Drip casting around a mandrel is a more conventional method of forming the primary shell of a breast implant. FIGS. 16-27 show different processes for forming viscoelastic membranes around mandrels.

With reference to FIGS. 16-27, methods of forming an elastomeric membrane by drip casting about a mandrel 117 are discussed herein. Generally, the inner zone 118 layers are formed on the mandrel 117. The mandrel 117 is then wasted, collapsed, or removed from the formed layers. There are many potential materials that can be utilized to form the mandrel 117. Gypsum plaster is a good example; however, various plastics could be employed as well. A plastic mandrel can be mechanically collapsed, softened with solvents, or heated to aid in removal without damaging the silicone castings. Gelatinous substances are another option that can provide sufficient stability to expand a membrane and form a mandrel that can be wasted and removed. Agar or agar-agar is one such form of a polysaccharide that can be molded into firm stable shapes. The possibilities for casting are extensive and different techniques may be employed for various applications of this invention.

In a preferred and non-limiting embodiment or aspect of a manufacturing process, after the formed membrane is removed from the mandrel 117, an expansion medium 122 is utilized to expand the formed layers during later steps of the casting process. Such a medium 122 is necessary to retain the previously cast membrane in a desired expanded state, as well as to support a membrane volume in a retracted state. The expansion medium 122 has many possible choices of materials and techniques of employment. Gasses and fluids under pressure are the simplest mediums that can be used. Agar and other materials that can be poured and cast to a fixed volume and shape can also be utilized. Agar has a low melting point, which allows it to be liquefied for removal or recast as required. Beads are another option that can produce fixed volumes of variable shapes. The advantages and disadvantages of various expansion mediums will be apparent based on the requirements of the particular stage of manufacture.

Figure 16:
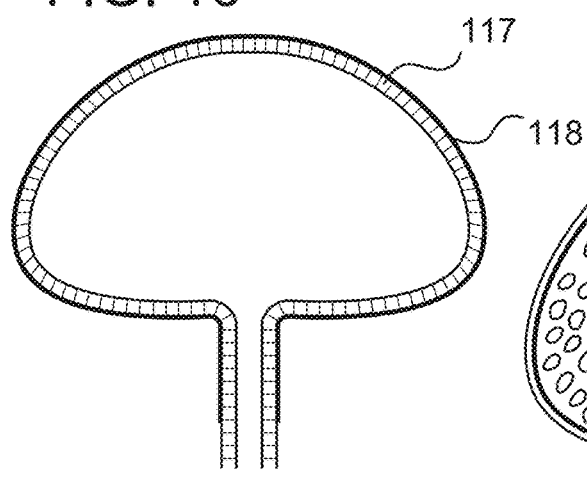
FIG. 16 is a cross-sectional view of a casting mandrel for forming an elastomeric membrane of an adjustable implant according to an aspect of the disclosure.

A first preferred and non-limiting manufacturing method using drip casting about a mandrel 117 is shown in FIGS. 16-19. FIG. 16 is a sectional view of the drip casting mandrel 117. The mandrel 117 is formed from a material that will be destroyed after the inner zone 118 layers are cast. Thus, the mandrel 117 can be described as a waste drip casting mandrel. The mandrel 117 can be cast in gypsum plaster. The gypsum plaster is a viable option, as it can be cast very thin and can be easily removed by mechanical means and/or dissolved with sodium bicarbonate and water. Multiple elastomeric layers are drip cast onto the mandrel 117 to form the inner zone 118 of the membrane. The inner zone 118 viscoelastic layers must be very durable, essentially impermeable, exhibit stable memory characteristics, and still remain very elastic.

Figure 17:
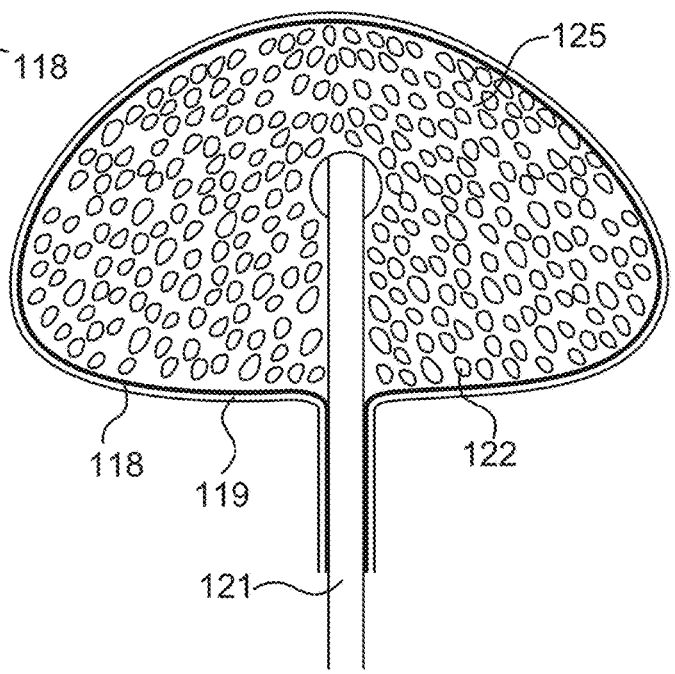
FIG. 17 is a cross-sectional view of a portion of an elastomeric membrane formed from the mandrel of FIG. 16, during a subsequent processing step, according to an aspect of the disclosure.

In FIG. 17, the mandrel 117 has been wasted and the inner zone 118 shell has been filled with expansion medium 122 through a filling tube 121 for the purpose of expanding the shell to a desired volume. The expansion medium 122 is required to be a stable medium that can be altered in volume. The filling tube 121 has three functions. It inflates the inner shell 118, allowing the expansion medium 122 to pass through it and fill the expanded volume. Once the desired form is achieved, the filling tube 121 becomes a supporting handle, which creates a drip casting mandrel to apply the middle zone 119 viscoelastic layers. The middle zone 119 layers are applied directly on top of the inner zone 118. The middle zone 119 layers have a tacky, but cured state, which remains soft and elastic. Such pliable characteristics allow these layers to be put in a state of compression.

Figure 18:
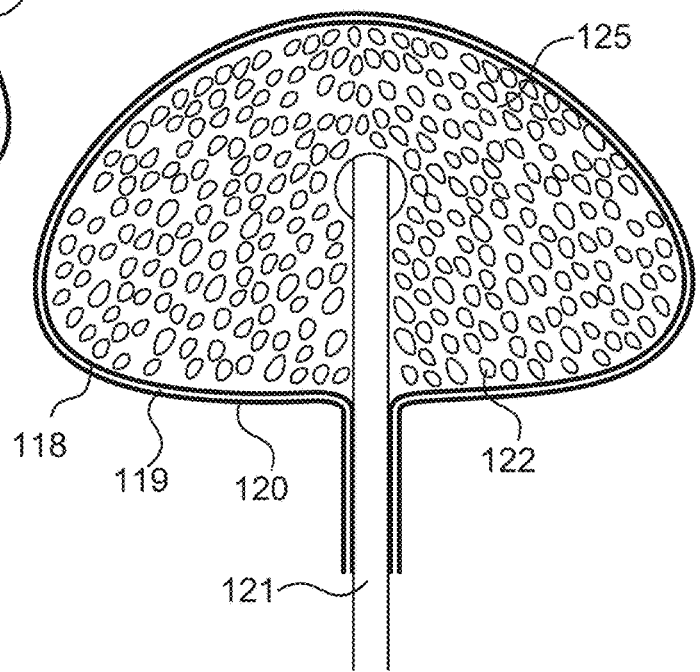
FIG. 18 is a cross-sectional view of a portion of the elastomeric membrane of FIG. 17, during a subsequent processing step according to an aspect of the disclosure.

FIG. 18 illustrates the third drip casting state. In this form, a portion of the expansion medium 122 has been removed to return the membrane to a volume and shape representative of the original mandrel 117. The filling tube 121 is utilized to create a vacuum retracting the inner zone layers and compressing the middle zone layers 119 to conform thereto. The outer zone 120 layers are drip cast to encase the middle 119 and inner zone 118 layers. The three-zone shell is complete when the outer zone 120 layers are cured. These outer zone 120 viscoelastic layers must be very durable, essentially impermeable, exhibit stable memory characteristics, and still remain very elastic. The layers of the outer zone 120 are essentially the same as, or similar to, the inner zone 118 viscoelastic layers.

Figure 19:
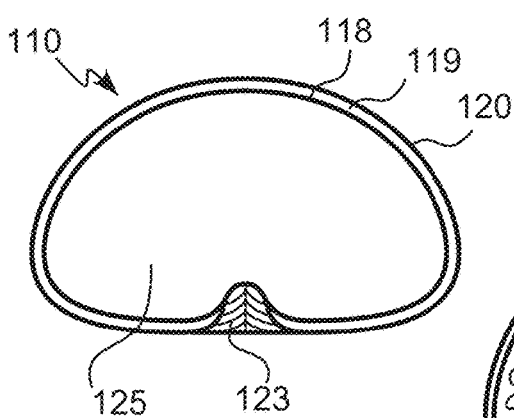
FIG. 19 is an adjustable implant formed from the elastomeric membrane of FIG. 18 according to an aspect of the disclosure.

FIG. 19 illustrates a non-limiting and preferred embodiment of the implant 110 formed from a three-zone membrane in its completed state. To produce the implant 110, the expansion medium 122 is removed producing a void shell. The shell is cleaned and surplus membrane, formed along the filling tube 121, is trimmed away. The flange remaining around the hole that remains in the middle of the posterior aspect of the implant is inverted inward and a plug 123 is cured to seal the implant 112. The plug 123 is formed from a viscoelastic material, similar to the material that forms the middle zone 119. The plug 123 functions as a self-sealing injection port that can be utilized to pre-fill a main chamber 125 of the implant 112 enclosed by the membrane to a desired volume prior to implantation. This plug 123 may take a variety of forms and configurations, such as a one-way valve, a flapper valve, an elastic valve, and the like. Further, the plug 123 may include one or more apertures or conduits through which to insert specified fluids into various areas of the implant 112. Biocompatible thickening agents can also be pre-filled prior to sealing the implant 112. The implant 112 is filled or partially filled with a fluid, such as saline, prior to implantation to a patient.

In another preferred and non-limiting embodiment or aspect, the mandrel 117 is an expandable structure which can be used for forming layers of the inner zone 118, expanded or middle zone 119, and, optionally, the outer zone 120. For example, an expandable mandrel 117 may be an inflatable balloon formed from a flexible rubbery material. Desirably, at least an outer surface of the expandable mandrel 117 is not formed from silicone to prevent portions of the implant membrane from adhering to the mandrel 117 during curing. A volume of the expandable mandrel 117 or balloon can be increased by inflating the mandrel 117 with a fluid (e.g., air or saline solution) to adjust the mandrel volume. For example, layers of the inner zone 118 may be formed around the mandrel 117 in the manner described hereinabove. After the layers of the inner zone 118 are cured, the mandrel 117 can be expanded by introducing fluid to the interior of the mandrel 117. Once the mandrel 117 is expanded, layers of the expanded or middle zone 119 can be formed around the expanded inner zone 118 in the manner described hereinabove. After the middle zone layers 119 are cured, the mandrel 117 can be collapsed by removing fluid from the interior of the mandrel 117, thereby reducing the volume of the mandrel 117 to a volume enclosed by the layers of the inner zone 118 at the time of curing. Once the mandrel 117 is collapsed, layers of the outer zone 120 can be formed over the middle zone 119 in the manner previously described by, for example, pouring liquid silicone over the layers of the middle zone 119. After the outer zone 120 is in place, the layers of the outer zone 119 can be cured. Following curing of the outer zone 120, the mandrel 117 can be collapsed or deflated and removed from mandrel 117 by, for example, sliding the collapsed or deflated mandrel through the opening of the formed elastomeric membrane.

Figure 20:
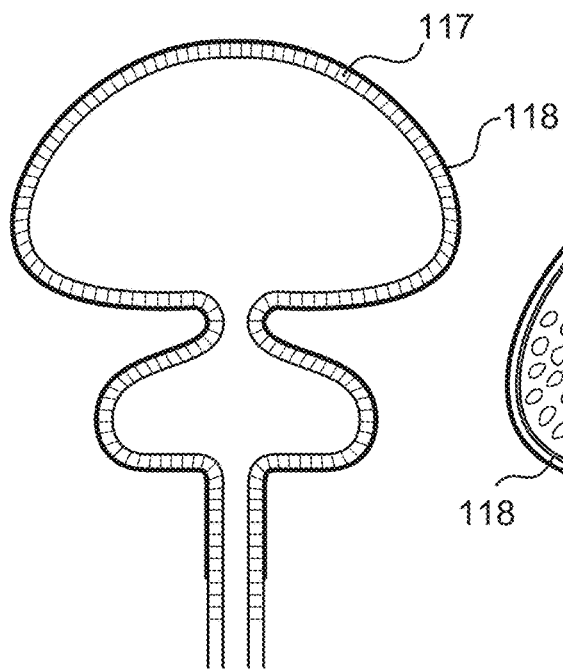
FIG. 20 is a cross-sectional view of a casting mandrel for forming an elastomeric membrane of an adjustable implant according to an aspect of the disclosure.

With reference to FIGS. 20-23, steps for forming another preferred and non-limiting embodiment of an implant by drip casting are illustrated. FIG. 20 is sectional view of a dual-chamber drip casting mandrel 117 used to form the inner zone 118 of the implant 112. The mandrel 117 is formed to a desired shape out of a material that will be destroyed after the inner zone 118 layers are cast to its form. The mandrel 117 can be described as a waste drip casting mandrel. The mandrel 117 can be cast in gypsum plaster. The gypsum plaster can be cast very thin and can be easily removed by mechanical means and/or dissolved with sodium bicarbonate and water. Multiple elastomeric layers are formed on the mandrel 117 to form the inner zone 118. The inner zone 118 viscoelastic layers must be very durable, essentially impermeable, exhibit stable memory characteristics, and still remain very elastic.

Figure 21:
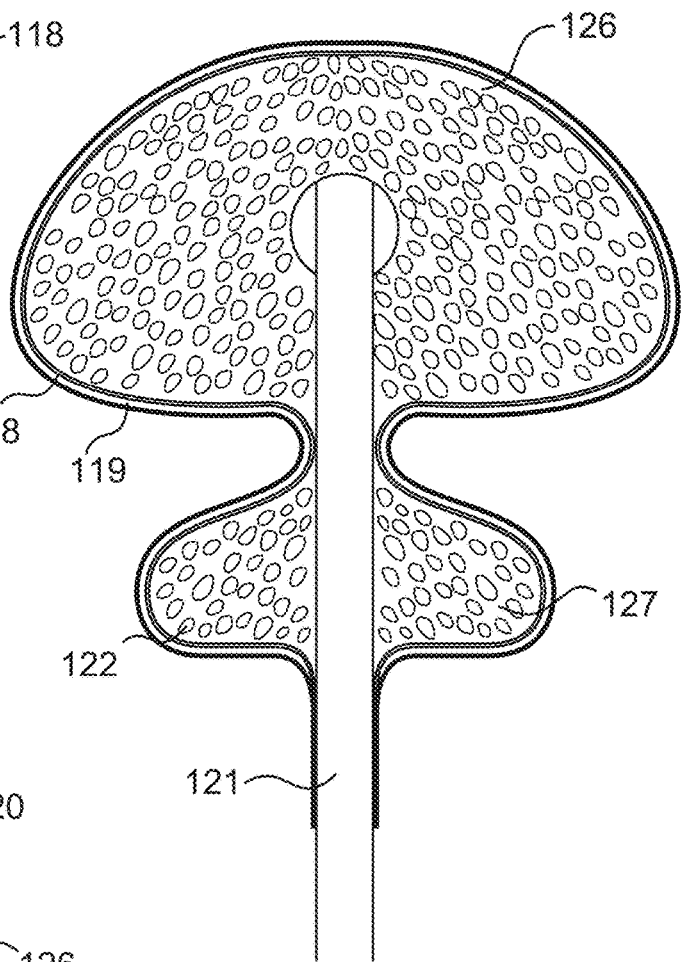
FIG. 21 is a cross-sectional view of a portion of an elastomeric membrane formed from the mandrel of FIG. 20, during a subsequent processing step, according to an aspect of the disclosure.

In FIG. 21, the dual chamber mandrel 117 has been wasted and both chambers of the inner zone 118 shell have been filled with the expansion medium 122 for the purpose of expanding the shell and retaining it to a desired volume. The filling tube 121 has three functions. It inflates the inner shell allowing the expansion medium 122 to fill the expanded volume. Once the desired form is achieved, the filling tube 121 becomes a supporting handle creating a drip casting mandrel to apply the middle zone 119 viscoelastic layers. The middle zone 119 layers are formed directly on the inner zone 118 and cured. As in previously described embodiments or aspects, the expanded or middle zone 119 layers attain a tacky, but cured state, which remains soft and elastic. Further, in some embodiments or aspects, pliable layers of the expanded or middle zone 119 are capable of being put in a compression state.

Figure 22:
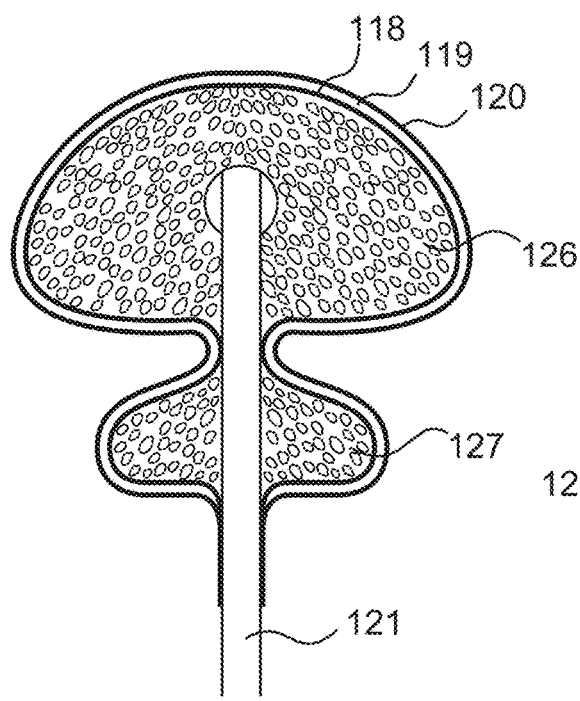
FIG. 22 is a cross-sectional view of a portion of the elastomeric membrane of FIG. 21, during a subsequent processing step according to an aspect of the disclosure.

FIG. 22 illustrates the third drip casting state. In this form, a portion of the expansion medium 122 is removed to return the membrane to a volume and shape representative of the original mandrel 117. The filling tube 121 is utilized to create a vacuum retracting the inner zone 118 layers and compressing the middle zone 119 layers to conform thereto. The outer zone layers 120 are drip cast to encase the middle 119 and inner zone 118 layers. The three-zone membrane is completed when the outer zone 120 layers are cured. These outer zone 120 viscoelastic layers must be very durable, essentially impermeable, exhibit stable memory characteristics and still remain very elastic. Thus, they are essentially the same as or similar to the inner zone 118 viscoelastic layers.

Figure 23:
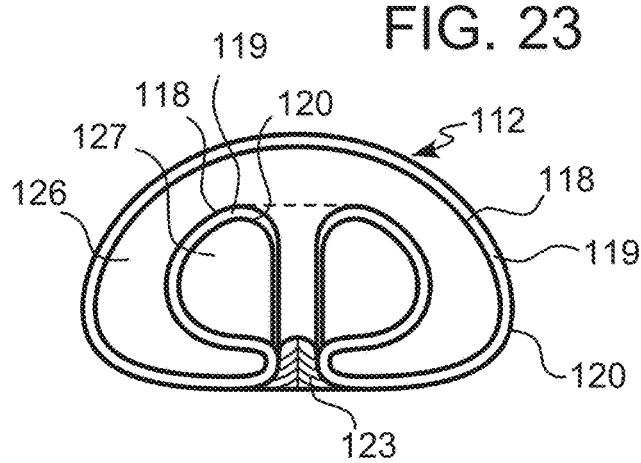
FIG. 23 is an adjustable implant formed from the elastomeric membrane of FIG. 22 according to an aspect of the disclosure.

FIG. 23 illustrates a preferred and non-limiting embodiment of the implant 112 in a completed state, formed from the elastomeric membrane depicted in FIGS. 21 and 22. To form the implant 112, the expansion medium 122 is removed producing a void shell. The shell is cleaned by appropriate measures. After cleaning, a smaller inner chamber 127 of the membrane is folded into an outer chamber 126, thereby forming an implant in which the outer chamber 126 encloses the inner chamber 127. Thus, the inner chamber 127 membrane is inverted in its final position. Further, a portion of the continuous membrane formed along the filling tube 121 becomes the termination of the membrane. As this portion of the membrane exits the posterior aspect the implant 112, surplus is trimmed away. Next, a plug 123 is inserted and cured to seal the implant 112. The plug 123 is formed from viscoelastic material similar to the middle zone 119. In some embodiments, the plug 123 functions as a self-sealing injection port that can be utilized to pre-fill the outer chamber 126 and inner chamber 127 of the implant to a desired volume prior to implantation. Biocompatible thickening agents can also be pre-filled prior to sealing the implant. In this final configuration, the implant 112 has a continuous viscoelastic membrane forming two self-sealing independent chambers. The implant 112 is filled or partially filled with a fluid, such as saline, prior to implantation to a patient.

With reference to FIGS. 24-27, a method of manufacture of another preferred and non-limiting embodiment or aspect of an adjustable implant 113 is illustrated. FIG. 24 is sectional view of a three-chamber drip casting mandrel 117 used for the initial forming of implant 113, according to a preferred and non-limiting embodiment or aspect of the invention. The mandrel 117 is formed to a desired shape out of a material that will be destroyed after the inner zone 118 layers are cast to its form. The mandrel 117 can be described as a waste drip casting mandrel 117. In some embodiments, the mandrel 117 can be cast in gypsum plaster. The gypsum plaster can be cast very thin and can be easily removed by mechanical means and/or dissolved with sodium bicarbonate and water. Multiple elastomeric layers are drip cast to the mandrel 117 to form the inner zone 118. The inner zone 118 viscoelastic layers must be very durable, essentially impermeable, exhibit stable memory characteristics, and still remain very elastic.

In FIG. 25, the three-chamber mandrel 117 is wasted and the main chamber of the inner zone 118 shell is filled with the expansion medium 122 for the purpose of expanding the shell and retaining it to a desired volume. The filling tube 121 requires a retaining clip 124 to seal the neck to the outer chamber 126 and also pull the two smaller chambers (collectively inner chamber 127) away from the outer chamber 126. The filling tube 121 has three functions. It inflates the inner zone 118 shell of the outer chamber 126 allowing the expansion medium 122 to pass through it and fill the expanded volume. Once the desired form is achieved, the filling tube 121 becomes a supporting handle creating a drip casting mandrel. The middle zone 119 viscoelastic layers are applied directly to portions of the inner zone 118. In a preferred and non-limiting embodiment, the middle zone 119 viscoelastic layer is only drip cast on the outer chamber 126. The middle zone 119 layers are required to attain a tacky, but cured state which remains soft and elastic. These pliable characteristics mean that the middle zone 119 layers can be placed in a state of compression.

FIG. 26 illustrates the third drip casting state. In this form, a portion of the expansion medium 122 is removed to return the outer chamber 126 to a volume and shape representative of the original mandrel 117. The expansion medium 122 is also added to the inner chambers 127 to fill them to a volume and shape representative of the original mandrel 117. The filling tube 121 is utilized to create a vacuum pressure, thereby retracting the entire structure and compressing the middle zone 119 layers to conform thereto. The outer zone 120 layers are drip cast to encase the middle zone 119 and inner zone 118 layers. The three-chamber shell is complete when the outer zone 120 layers are cured. These outer zone 120 viscoelastic layers must be very durable, essentially impermeable, exhibit stable memory characteristics, and still remain very elastic. They are essentially the same as or similar to the inner zone 118 viscoelastic layers. The final three-chamber shell consists of an outer chamber 126 shell which has the three layer self-sealing properties. The two smaller chambers (collectively inner chambers 127) only include inner zone 118 and outer zone 120 layers.

FIG. 27 illustrates another preferred and non-limiting embodiment or aspect of an implant 113 formed from the membrane layers of FIGS. 25 and 26, in its completed state. In order to produce the completed implant 113, expansion medium 122 is removed producing a void shell. The shell is cleaned through appropriate measures. The two smaller chambers (collectively inner chambers 127) are folded into the outer chamber 126. Thus, the inner chamber 127 membrane has an inverted outer aspect and non-inverted inner aspect in its final position. A portion of the continuous membrane along the filling tube 121 forms the ends of the membrane. A port for accessing the outer chamber 126 of the membrane is positioned at the ends of the membrane. Surplus material is trimmed from this portion of the membrane. A plug 123 is inserted and cured to seal the implant 113 in the port. As in previous embodiments, the plug 123 can be formed from viscoelastic material similar to the middle zone 119. The plug 123 functions as a self-sealing injection port that can be utilized to pre-fill the outer chamber 126 and inner chamber 127 of the implant 113 to a desired volume prior to implantation. Biocompatible thickening agents can also be pre-filled prior to sealing the implant. It is noted that the inner chamber 127 may be perforated to allow fluid communication of all chambers. In this embodiment, inner structures of the implant 113, namely the inner chamber 127, provide baffling characteristics to calm fluid motion of the liquid utilized to fill the chambers. The implant 113 is filled or partially filled with a fluid, such as saline, prior to implantation to a patient.

Figure 28:
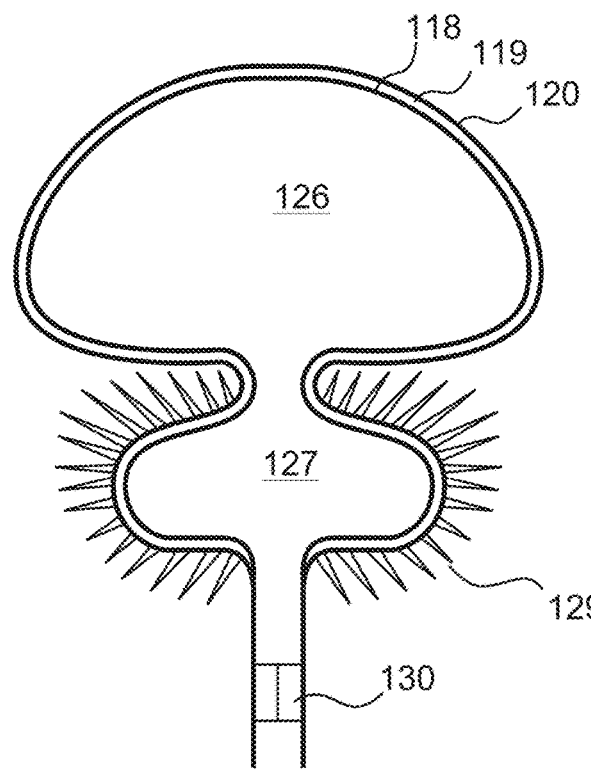
FIG. 28 is a cross-sectional view of an elastomeric membrane for an adjustable implant according to an aspect of the disclosure
Figure 29:
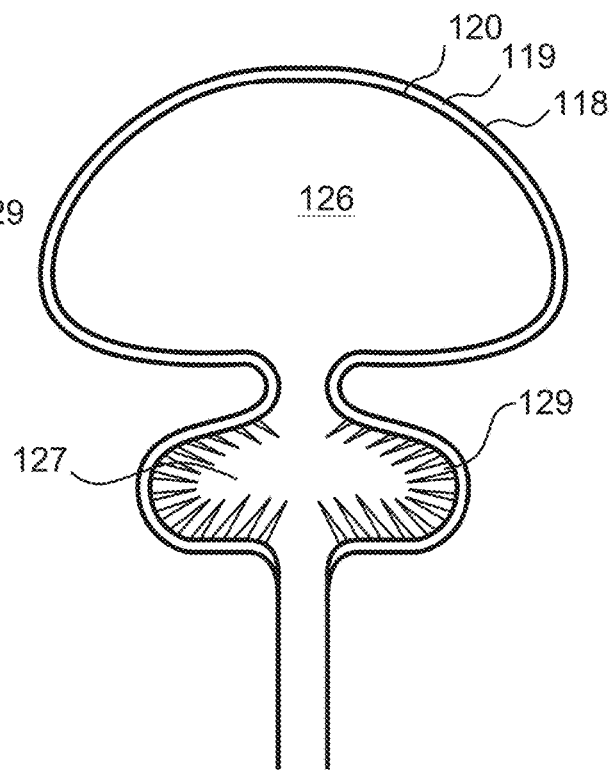
FIG. 29 is a cross-sectional view of the elastomeric membrane of FIG. 28 in an inverted position according to an aspect of the disclosure.
Figure 30:
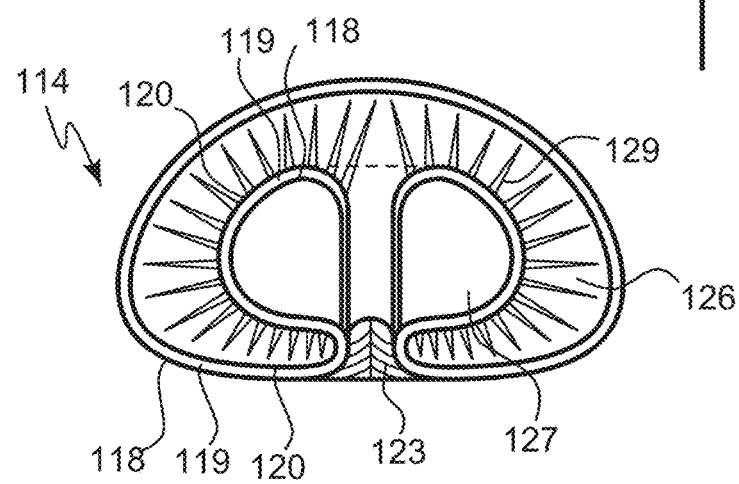
FIG. 30 is a cross-sectional view of an adjustable implant formed from the elastomeric membrane of FIG. 28 according to an aspect of the disclosure.

With reference to FIGS. 28-30, steps for forming an adjustable implant 114 according to another preferred and non-limiting embodiment or aspect of the invention are illustrated. FIG. 28 depicts a completed shell formed by drip casting around a mandrel, including inner zone layers 118, middle layers 119, and outer zone layers 120. In FIG. 28, the expansion medium 122 is removed producing a void shell. The shell is cleaned after the expansion medium 122 is removed. The shell is inflated enough to maintain its shape and a temporary plug 130 is positioned near an opening of the shell. Viscoelastic tendrils 129 are formed and cured on one of the chambers of the shell.

FIG. 29 depicts the next formation stage, where the entire membrane is inverted upon itself, such that tendrils 129 extend inward into the inner chamber 127. The final configuration of the implant 114 with tendrils 129 is illustrated in FIG. 30. The smaller inner chamber 127 with tendrils 129 is folded into the outer chamber 126. The inner chamber 127 is not inverted in its final position. The tendrils 129 expand into the outer chamber 126 providing stability to the final form and baffling characteristics to calm fluid motion in the outer chamber 126. The outer chamber 26 membrane remains inverted in its final position. A portion of the continuous membrane formed along the filling tube 121 forms the termination of the membrane. As this portion of the membrane exits the posterior aspect of the implant 113, the surplus membrane material is trimmed. As in previously described embodiments, a plug 123 is inserted and cured to seal the implant 114. For example, the plug 123 can be formed from viscoelastic material similar to the middle zone 119. The plug 123 functions as a self-sealing injection port that can be utilized to pre-fill the outer chamber 126 and inner chamber 127 of the implant 114 to a desired volume prior to implantation. Biocompatible thickening agents can also be pre-filled prior to sealing the implant. This final configuration of the implant 114 has a continuous viscoelastic membrane forming two self-sealing independent chambers, namely an outer chamber 126 and an inner chamber 127. The implant 114 is filled or partially filled with a fluid, such as saline, prior to implantation to a patient.

Exemplary Implant Filled With a Cohesive Gel

Figure 31:
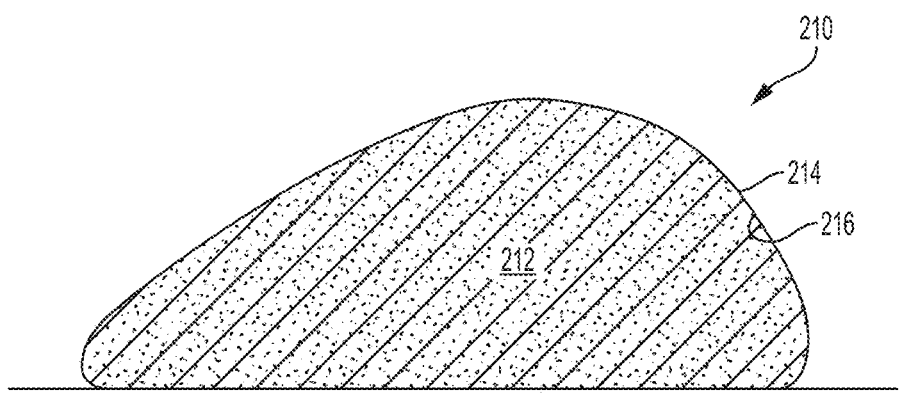
FIG. 31 is a schematic cross sectional view of another exemplary elastomeric implant according to an aspect of the disclosure.

In another preferred and non-limiting embodiment or aspect of the invention, with reference to FIG. 31, an implant 210 includes a cohesive gel 212 enclosed in an elastomeric shell or membrane 214. The gel can be inserted into the membrane or shell in a flowable state and cured to impart cohesive properties to the implant 210. An example of a cohesive gel 212 that can be used with the implant 210 is a cross-linked dimethyl silicone gel. The membrane 214 can be any of the membranes discussed herein including, for example, a membrane with intrinsic compression (e.g., the two-zone membrane or a three-zone membrane discussed herein), a membrane without intrinsic compression, and/or a pre-stressed membrane. Desirably, the elastomeric shell or membrane 214 exerts a contracting force on the cohesive gel 212 which is balanced by outwardly directed forces of the gel 212 to form a stable implant structure. As in previously described examples, the shell or membrane 214 is formed from a plurality of laminated layers of an elastomeric material, such as silicone. One or more of the layers can be continuous layers which entirely enclose the gel 212.

In a preferred and non-limiting example, the elastomeric shell or membrane 214 is a single zone membrane without intrinsic compression. The shell or membrane 214 can be between about 0.75 mm to 5.0 mm thick, preferably between 1.0 mm and 3.0 mm thick, and more preferably between 1.8 mm and 2.5 mm thick. However, shells having a thickness of greater than 5.0 mm may be used for particular applications. Layers of the elastomeric shell or membrane 214 can have a Shore hardness of about Shore 00-10 to Shore A-40.

In a single-zone membrane without intrinsic compression, all of the layers of the shell or membrane 214 are formed around a single mandrel (e.g., for drip casting) or in a single mold (e.g., using the reverse casting method). Thus, unlike in previously-described embodiments, the membrane 214 may not have intrinsic compression. For example, outer or inner layers or zones of the membrane 214 may not exert contracting forces on middle layers or zones of the membrane 214, as occurs in other membranes and shells discussed herein. Instead, the elastomeric membrane 214 is configured to exert a contracting force on the gel 212. As a result, a volume enclosed by the elastomeric membrane 214 when cured is smaller than the volume of the gel 212. The volume enclosed by the membrane 214 when cured is also smaller than a volume of the finished implant 210, such that in a finished state, the elastomeric membrane 214 exerts the contracting force to the gel 212. For example, the volume enclosed by the shell or membrane 214 when cured may be about 50% to 95%, and preferably about 80%, of the volume of the finished implant 210. In order to obtain such balanced compression, the volume of the elastomeric shell or membrane 214 when formed can be expanded by about 5% to about 50% and preferably about 20% prior to providing the gel 214 to the interior of the implant 210.

In some examples, the shell or membrane 214 is formed from simple layers of uniform hardness. In other preferred and non-limiting embodiments or aspects, the membrane 214 may be formed from multiple layers of variable hardness. For example, the layers may decrease in hardness from the outermost layers towards an inner surface 216 of the membrane 214. In that case, the innermost layers of the membrane 214 would be soft. Softer layers have properties which are more similar to the properties of the cohesive gel 212. Silicone materials bond better with layers having similar properties (e.g., hardness), such that that a membrane 214 with softer innermost layers bonds more securely with the cohesive gel 212. Accordingly, the membrane 214 can be designed so that the layers transition slowly to a soft state similar to the gel 212 to ensure superior bonding. In some instances, innermost layers of the membrane 214 can include layers with some gel-like properties. In some examples, outermost layers of the membrane can be a hardness of about Shore A-20 to Shore A-40 Shore. Innermost layers of the membrane can have a hardness of about Shore 00-10 to Shore A-20.

In some examples, the gel 212 is a cohesive gel having form stable or substantially form stable properties. For example, the gel 212 can be a silicone gel which can be cured by applying heat to the filled implant 210. Exemplary gel materials that can be used to fill a cohesive gel implant are described, for example, in U.S. Pat. No. 4,455,691, entitled "Silicone gel filled prosthesis" and in U.S. Pat. No. 8,858,630, entitled "Variable cohesive gel form-stable breast implant", each of which is incorporated by reference in its entirety. Other soft polymer materials may also be used for the gel 212 including, for example, polyesters, polyacrylamides, and others. Exemplary materials are described in U.S. Pat. No. 5,941,909, entitled "Filling material for soft tissue implant prostheses and implants made therewith", which is incorporated by reference in its entirety.

An exemplary method for forming a gel filled elastomeric implant 210 including a single-zone membrane 214 without intrinsic compression is shown in FIGS. 32A-32E. FIGS. 32A-32C show steps for producing a single-zone elastomer shell or membrane 214 by the reverse casting method discussed herein. In other examples, the single zone shell or membrane may be formed by drip casting over a mandrel as discussed hereinabove.

As shown in FIG. 32A, a mold 218 is provided. The mold 218 can be similar in form to molds discussed hereinabove in connection with the reverse casting processing for the multi-zone membrane. In some examples, the mold 218 may define an inner cavity that is the same shape as the finished implant, but smaller. For example, the volume of the cavity of the mold 218 may be between 50% and 95%, and preferably about 80%, of the volume of the finished implant. When the mold 218 is the same shape as the finished implant, the membrane expands equally and uniformly to conform to the shape of the finished implant. In other examples, the mold 218 may be a different shape than the finished implant. For example, the mold 218 may define a simple round form or another form that is capable of expanding into the shape of the finished implant. In some examples, the shape of the mold 218 may be selected such that, when expanded, the membrane produces variable contractile forces against the soft gel. For example, top and bottom portions of the membrane may be configured to exert increased contractile forces on the gel, such that equatorial portions of the finished implant bulge or have increased resiliency.

The mold 218 can include a textured interior surface 220 for producing a textured implant. The mold 218 can be a flexible and disposable single use product. In other examples, multi-use molds formed from more rigid materials can also be used within the scope of the present disclosure. As shown in FIG. 32B, a flowable elastomeric material, such as silicone, is injected or poured into the mold 218 to form an outermost layer of the shell or membrane 214. For example, the elastomeric material may be poured into the mold 218 through a narrow opening 222. The elastomeric material can be dispersed on the textured surface 220 of the mold 218 by oscillating or rotating the mold 218. The deposited elastomeric material dries or becomes form stable. The process can then be repeated multiple times to deposit multiple layers on the inner surface of the mold. As discussed herein, the hardness of the layers can be modified to produce a membrane 214 of variable hardness. For example, the inner most layers of the membrane 214 may be softer than the outermost layers of the membrane 214. Once the multiple layers of elastomeric material are deposited on the interior surface 220 of the mold 218, the elastomeric material can be cured or partially cured to form the single-zone shell or membrane 214. As previously described, the process of depositing and curing the elastomer material can be carried on multiple times to produce a laminated multi-layer shell. In some examples, the cured shell or membrane 214 remains open, as shown in FIG. 32B, so that the implant can be filled by pouring gel through the opening. In other examples, the shell or membrane 214 can be closed to form a continuous membrane. A continuous membrane can be stronger and less prone to leaks than membranes having an opening covered by a patch or plug.

As shown in FIG. 32C, after being cured or partially cured, the single-zone shell or membrane 214 is removed from the mold. In other cases, the shell or membrane 214 can be formed by drip casting on a mandrel as described hereinabove.

As shown in FIG. 32D, the shell or membrane 214 is expanded to a finished shape. For example, as shown in FIG. 32D, the membrane 214 can be placed in a vacuum chamber mold 224 having a rigid-set form defining a cavity with the desired shape of the implant. The vacuum chamber mold 224 is actuated, thereby causing the shell or membrane 214 to expand to an enlarged volume and to assume the shape of the mold cavity. For example, a valve 226 can be opened and a pump can be engaged to evacuate air from the mold 224 to create a negative pressure in the mold 224.

In other preferred and non-limiting embodiments or aspects, the membrane 214 can be expanded by pressurizing the inner cavity or volume of the membrane 214 rather than by application of vacuum force. For example, an opening 228 of the membrane 214 can be connected to a pump or device to inflate the membrane 214. As the membrane 214 inflates, it can be pressed against a mold, thereby causing the membrane 214 to conform to the shape of the mold. In some preferred and non-limiting embodiments or aspects, expanding the shell or membrane 214 involves expanding an interior volume of the shell or membrane 214 by about 5% to about 50% prior to filling the shell or membrane 214 with the cohesive gel 212. In one preferred embodiment, the shell or membrane 214 is expanded by about 20% prior to filling the membrane 214 with the cohesive gel 212. It is noted that for embodiments including the cohesive gel 212, the degree of expansion of the shell or membrane 214 is generally less than is needed for forming a multi-zone membrane with intrinsic compression as show and described in connection with FIGS. 6-15. Further, in some embodiments, the degree of expansion of the shell or membrane 214 is selected such that, once vacuum force is removed, the formed implant 210 returns to a size which is slightly larger than the membrane 214 when formed. For example, in its completed state, the membrane 214 may enclose a volume which is preferably between about 10% and 40% larger than the volume enclosed by the membrane 214 when originally formed.

As shown in FIG. 32E, while the vacuum pump remains active and the shell or membrane 214 remains in its expanded state, the shell or membrane 214 is filled with a filling material, such as a flowable cohesive gel 212. For example, the flowable gel can be poured through the opening 228. After the membrane 214 is filled to a desired volume, the opening 228 can be closed or covered, for example, by folding overlapping portions of the shell or membrane 214 against each other to enclose the gel 212. In other examples, an elastomeric plug may be placed in the opening 228 to enclose the gel 212.

If the membrane 214 is an enclosed continuous membrane, the implant can be filled by injection. For example, an injection needle can be inserted through the membrane 214. A second needle for evacuating air from the membrane 214 can be inserted through another portion of the membrane 214. Once the needles are in place, fluid, such as the flowable cohesive gel, can be injected into the implant. As the filling material enters the implant, air is evacuated through the second needle.

Once the membrane 214 is closed, the flowable gel 212 can be cured thereby causing the gel 212 to transition to a form-stable, cohesive state. For example, the gel 212 can be cured by applying heat to the gel 212 and membrane 214. In some examples, the curing temperature for cohesive gel is between about 110° C. and 170° C. In other examples, curing may be initiated using other common techniques, such as application of electromagnetic radiation, UV radiation, or by adding a curing agent to the flowable gel material. Curing the gel 212 also effectively bonds the gel 212 to the innermost layers of the membrane 214. As discussed herein, in some examples, innermost layers of the membrane 214 can have soft, gel-like properties to improve the bond between the gel 212 and membrane 214.

The finished implant 210 generally has the shape of the vacuum chamber mold 224. Further, since the shell or membrane 214 is expanded while being filled with the cohesive gel 212, the shell or membrane 214 exerts the contracting force against the gel 212. Once cured, the form-stable, cohesive structure of the gel 212 counteracts the contracting force, thereby contributing to the resiliency and softness of the finished implant.

Exemplary Implants Formed From Preformed Shells

With reference to FIGS. 33A-35B, according to another preferred and non-limiting embodiment or aspect of the disclosure, a multi-zone implant, such as a two zone implant 310 or a three zone implant 410, can be formed from a preformed elastomeric shell 312, 412, such as a preformed elastomeric shell 312, 412 used in production of conventional commercially available implants. In these embodiments, the preformed shell 312, 412 is used in place of the outer zone of previous embodiments to provide support or structure for the implant. Such preformed shells 312, 412 are generally formed around a mandrel and comprise multiple laminated layers of an elastomeric material, such as silicone. The preformed shell 312, 412 are generally less than 1.5 mm thick, or preferably from about 0.25 mm to 1.0 mm thick. Layers of the elastomeric shell or membrane can have a Shore hardness of about Shore A-20 to Shore A-40. The preformed shell can enclose an interior volume of about 80 cc to 800 cc.

The preformed shell 312, 412 generally includes only a single zone of elastomeric layers, meaning that all of the layers of the shell 312, 412 are formed around the same mandrel or in the same mold. When forming the preformed shell 312, 412, a volume of the mandrel or mold used to form the preformed shell does not change as the layers are formed and cured, as occurs in other methods of forming an implant shell disclosed herein. Instead, the elastomeric layers are applied over top of one another on the mandrel or mold and permitted to cure to form the shell. Single-zone preformed shells, which can be used to form the implant disclosed herein, are available commercially from manufacturers including, for example: Mentor Worldwide LLC of Irvine, Tex.; Allergan PCL of Madison, N.J.; Sientra, Inc. of Santa Barbara, Calif.; and Polytech Health & Aesthetics GmbH of Dieburg, Germany.

Method of Forming a Two-Zone Implant From a Preformed Shell

Figure 33A:
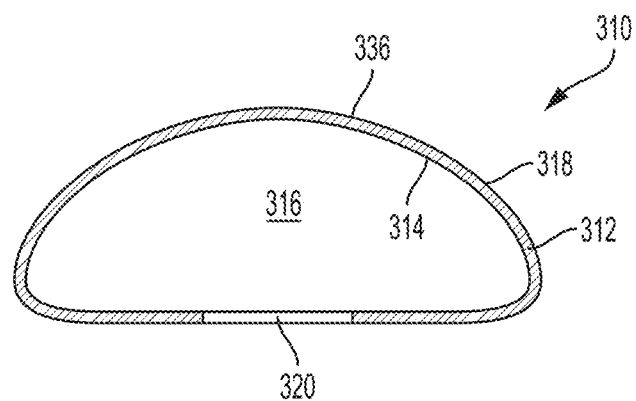
FIGS. 33A-33E are schematic drawings illustrating an exemplary process for forming a two-zone implant from a preformed shell, according to an aspect of the present disclosure.
Figure 33B:
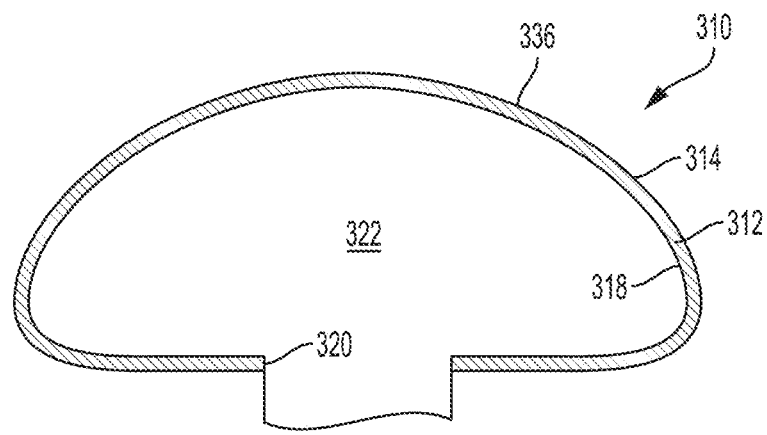

In some preferred and non-limiting aspects or embodiments, a method of forming an implant 310 for volumetrically altering, replacing, expanding, or augmenting body tissues from the preformed shell 312 includes providing the preformed shell 312. In its finished form, the shell 312 includes a two-zone elastomeric membrane having an inner surface 330 and an outer surface 336. As shown in FIG. 33A, the preformed shell 312 has an inner surface 314 partially enclosing an interior volume 316, an outer surface 318, and an opening 320 for accessing the interior volume. The opening 320 is generally about 2.5 cm to 4.5 cm in diameter, though many different sized openings can be used within the scope of the present disclosure. The preformed shell 312 can be formed from at least one cured elastomeric layer or from a plurality of laminated elastomeric layers. As shown in FIG. 33B, the method includes inverting the preformed shell 312 and expanding the interior volume 316 of the inverted preformed shell 312 to an expanded volume, in which the interior volume of the shell 312 is greater than a volume of the preformed shell 312 at a time of forming the shell 312. For example, expanding the shell 312 may include expanding the interior volume of the shell by between 50% and 800%, preferably about 500%, compared to the volume of the shell 312 at the time of forming the shell 312. As in previously described examples, a volume of the elastomeric shell 312 can be expanded using a mandrel or mold. For example, the inverted shell 312 can be placed over a mandrel 322, such that the outer surface 318 of the preformed shell 312 contacts the mandrel 322, to place the shell 312 in an expanded state.

Figure 33C:
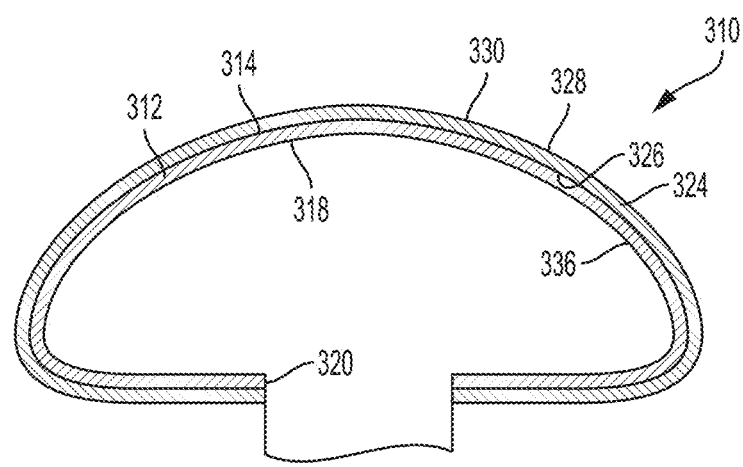

After the preformed shell 312 is placed on the mandrel 322, as shown in FIG. 33C, an inner zone 324 including at least one inner elastomeric layer is formed on the inner surface 314 of the shell 312, while the shell 312 is in the expanded state. For example, one or more layers of the elastomeric material, such as silicone, can be formed on top of one another to form the inner zone 324. Generally, elastomeric layers are formed by either spraying or applying the silicone material to a surface and permitting the applied layers to cure. In some examples, the elastomeric layers of the inner zone 324 are softer than layers of the preformed shell 312. For example, layers of the inner zone 324 can have a Shore hardness from about Shore 00-10 to about Shore A-20 and, for example, can be formed by blending Shore 00-10 and Shore A-20 materials to form the inner zone 324. The inner zone 324 may be from about 0.2 mm to about 3.5 mm thick. In that case, the completed two-zone elastomeric membrane has a total thickness of about 0.7 mm to about 4.5 mm In some examples, the elastomeric layers of the inner zone 324 are substantially similar in material composition. In other examples, material properties of the different layers can vary to produce an inner zone 324 with variable hardness and/or elasticity. For example, a proximal-most layer 326 of the inner zone 324 (e.g., a layer of the inner zone 324 nearest to the preformed shell 312) and distal-most layers 328 (e.g., layers farthest from the preformed shell 312, which form an inner surface 330 of the implant 310) can be formed from firmer materials, such as from a blend of an amount of Shore 00-10 and Shore A-20 materials. In some examples, firmer layers may make up about 10% to 20% of a total volume of the inner zone 324. Interior layers of the inner zone 324 can be blended (e.g., a blend of Shore A-10 elastomer and Shore 00-10 elastomer), becoming progressively softer moving towards a middle of the inner zone 324. Layers near a middle of the inner zone can be soft. For example, middle layers near the middle of the inner zone 324 can have a hardness of Shore 00-10. In general, the blended and softer layers of the inner zone 324 can make up about 80% to 90% of the total volume of the inner zone 324.

Figure 33D:
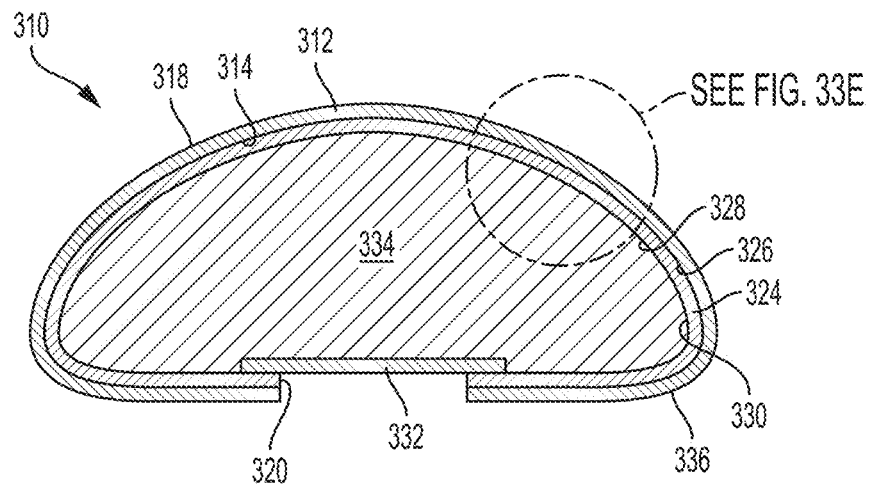
Figure 33E:
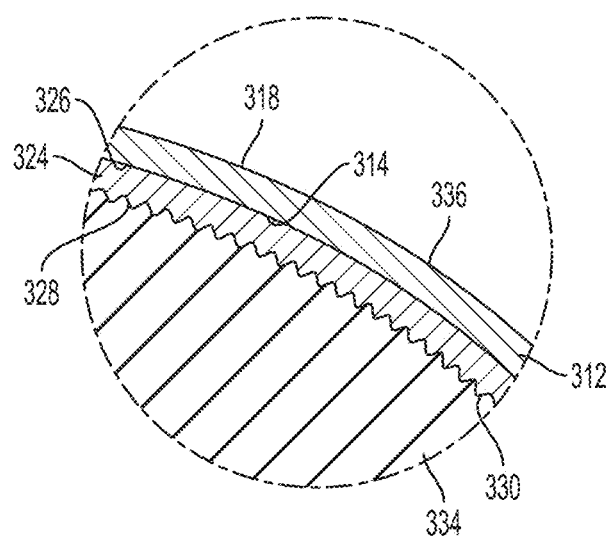

As shown in FIG. 33D, after the layers of the inner zone 324 cure, the shell 312 (which can be referred to as a multi-zone shell, since it includes both the preformed shell 312 and inner zone 324) is removed from the mandrel 322 and inverted back to its original orientation. Once removed from the mandrel 322, the shell 312 naturally retracts to a smaller volume, closer to the volume of the preformed shell 312 when originally formed (as shown in FIG. 33A). In this retracted position, the pre-formed shell 312 exerts a contracting force on the elastomeric layer(s) of the inner zone 324. Since the layers of the inner zone 324 are formed when the preformed shell 312 is in the expanded state, contracting the inner zone 324 compresses layers of the inner zone 324. Such compression causes the layers of the inner zone 324 to fold, creating texturing or a textured region having ridges, grooves, and crevices on the inner surface 330 of the implant 310. FIG. 33E shows an expanded view of the shell 312 including the texturing on the inner surface 330 of the implant 310.

After the shell 312 is inverted and retracts to about its original volume, a completed implant can be formed. In order to form the completed implant, as shown in FIG. 33D, the shell 312 is enclosed to form at least one chamber, in a similar manner as in previous embodiments. For example, a piece of elastomeric material, such as a plug or patch 332, can be vulcanized to the outer surface 336 and/or, preferably, to the inner surface 330 of the shell 312 to cover the opening 320 to fully enclose the interior volume 316 of the implant 310. In some examples, forming the implant 310 can also include filling the implant 310 with a fluid, such as saline solution or a cohesive gel 334. When a cohesive gel 334 is used as a filling material, in an uncured state, the gel 334 can be sufficiently fluid to flow into the ridges, grooves, and crevices on the textured inner surface 330 of the implant 310. As the gel 334 cures, it adheres to the textured inner surface 330, which creates a more stable interface between the gel 334 and the layers of the inner zone 324 than if texturing were not present. Specifically, since the textured inner surface 330 has more surface area than a flat surface enclosing a similar volume, the cohesive gel 334 is better able to adhere to the inner surface 330, than if texturing were not present. As a result of the stable interface, mechanical properties of the shell 312 and implant 310 are improved. For example, as a result of adhesion between the gel 334 and textured inner surface 330, a likelihood of delamination of the gel 334 and inner surface 330 of the shell 312 is reduced. Accordingly, the formed implant 310 is better able to maintain its shape, giving the completed implant 310 a more natural appearance and feel. Delamination of the shell 312 and gel 334 can also occur when there is a substantial difference in material properties between the inner surface 330 of the shell and the gel 334. Therefore, it is desirable that the distal-most layers 328 of the inner zone 324 are a more similar in hardness to the cohesive gel 334 than are layers of the pre-formed portion of the shell 312.

Method of Forming a Three-Zone Implant From a Preformed Shell

Figure 34A:
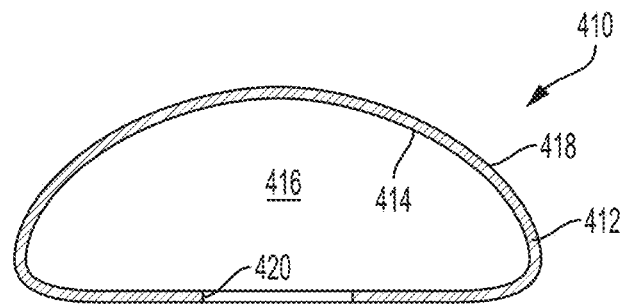
FIGS. 34A-34D are schematic drawings illustrating an exemplary process for forming a three-zone implant from a preformed shell, according to an aspect of the present disclosure.
Figure 34B:
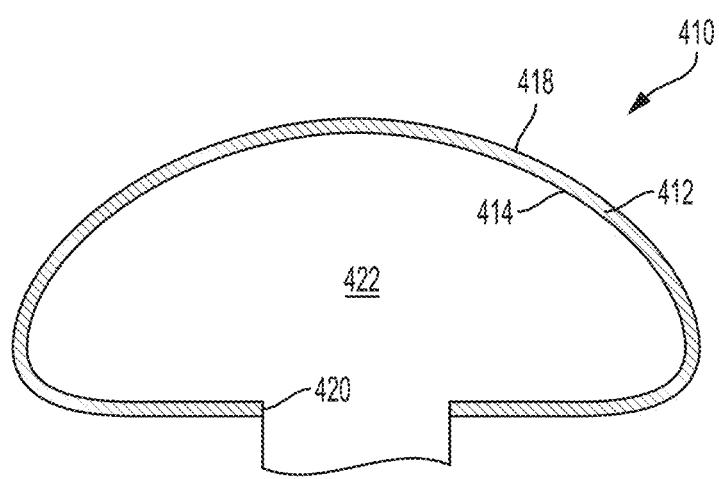
Figure 34C:
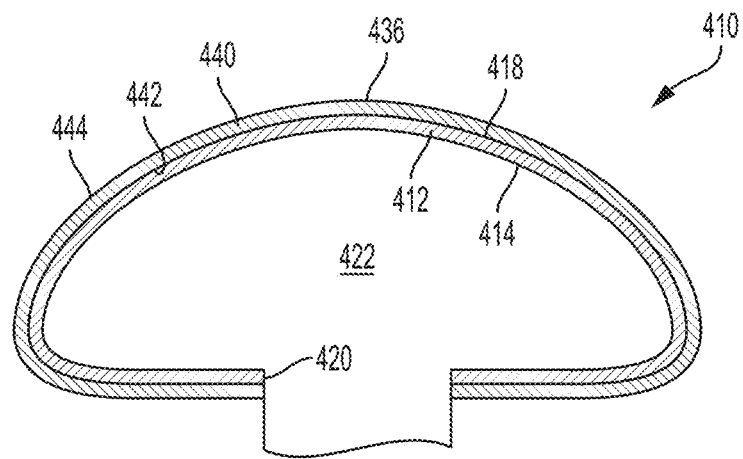

According to another preferred and non-limiting aspect or embodiment of the present disclosure, steps for forming the three-zone implant 410 from a preformed shell 412 including an elastomeric membrane having a textured inner surface 430 and a textured outer surface 436 are shown in FIGS. 34A-34D. In order to form the implant 410, as in the previous example, a commercially available preformed shell 412 is provided, as shown in FIG. 34A, and transformed to an expanded state, as shown in FIG. 34B. For example, the preformed shell 412 can be placed over a mandrel 422, such that an inner surface 414 of the shell 412 contacts the mandrel 422. With the shell 412 in the expanded state, as shown in FIG. 34C, an outer zone 440 including at least one outer elastomeric layer is formed on at least a portion of an outer surface 418 of the preformed shell 412. For example, as in previous embodiments, a plurality of layers of elastomeric material can be deposited on the surface 418 of the shell 412 and laminated to form the outer zone 440 of elastomeric layers. In general, layers of the outer zone 440 are firmer than layers of the inner zone 324 (shown in FIGS. 33A-33E). For example, layers of the outer zone 440 may have a hardness of from Shore 00-30 to Shore A-20. The outer zone 440 can be from about 0.1 mm to about 1.0 mm thick. In that case, a shell of the three-zone implant 410 can have a total thickness of from about 0.8 mm to 5.0 mm In some examples, the layers of the outer zone 440 are formed from materials having differing material properties. For example, a proximal-most layer 442 (e.g., a layer closed to the preformed shell 412) and a distal-most layer 444 (e.g., the layer farthest from the preformed shell 412) may be formed form firmer materials, while layers in a middle of the outer zone 440 can be softer.

Figure 34D:
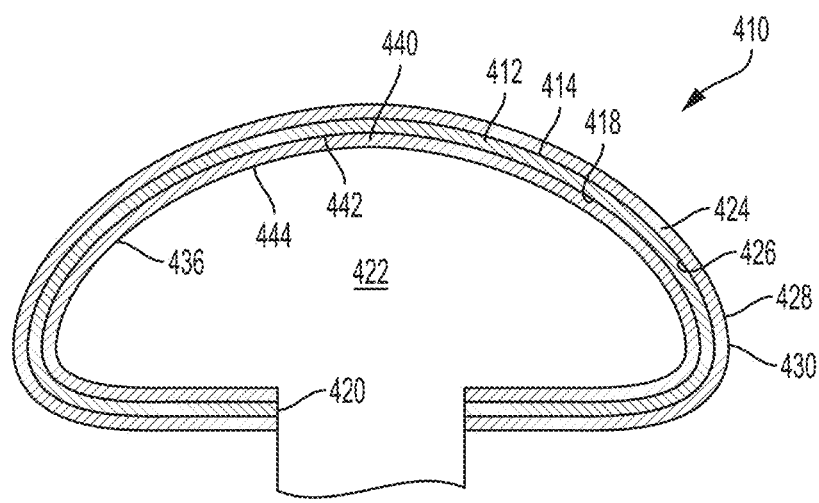

After the layers of the outer zone 440 cure, the shell 412 (which can be referred to as a multi-zone shell, since it includes the preformed shell 412 and outer zone 440) can be removed from the mandrel 422 or mold and inverted, such that the inner surface 430 of the implant 410 faces outward. The shell 412 is then expanded again either using a mold or by placing the shell on a mandrel 422 in the inverted orientation, such that the outer surface 436 of the implant 410 contacts the mandrel 422. Once the shell 412 is mounted to the mandrel 422 in its inverted orientation, as shown in FIG. 34D, an inner zone 424 including at least one inner elastomeric layer can be formed by applying elastomeric layers to the shell 412. The mandrel 422 used for forming the inner zone 424 has a volume that is greater than a volume enclosed by the preformed shell 412 at the time of forming the shell 412. In some examples, the mandrel 422 used for forming the inner zone 424 is the same as the mandrel 422 used for forming the outer zone 440. In other examples, the mandrels 422 used for forming the inner zone 424 and the outer zone 440 may be different volumes to vary the compression or contraction forces applied to the zones 424, 440 by the preformed shell 412. As in the previous example, the inner zone 424 can include a plurality of elastomeric layers having the same hardness or varying hardness. Generally, the inner zone 424 is softer than the outer zone 440 or the preformed shell 412. For example, the layers of the inner zone 424 can have a hardness of from about Shore 00-10 to about Shore A-20.

After the inner zone 424 is formed, the shell 412 (which is a multi-zone shell with three distinct zones) is removed from the mandrel 422 and inverted back to its original position, as shown in FIG. 34A. Removing the shell 412 from the mandrel 422 allows the shell 412 to retract to a volume closer to a volume of the preformed shell 412 when formed. In this orientation, the preformed shell 412 exerts a retracting force on layers of the outer zone 440 and compresses layers of the inner zone 424, thereby causing the shell 412 to adopt a volume less than a volume of the mandrel 422. The retraction of the layers of the outer zone 440 and compression of layers of the inner zone 424 causes the layers of the inner zone 424 and the outer zone 440 to fold upon one another, thereby producing textured regions on the inner surface 430 and the outer surface 436 of the implant 410. A detailed cross-sectional view of the shell 412 including the textured inner and outer surfaces 430, 436 is shown in FIG. 35B.

Once the shell 412 is completed, the implant 410 is formed by enclosing the shell 412 to form at least one chamber. For example, as in previous examples, the opening 420 of the shell 412 can be enclosed by attaching and/or vulcanizing a piece of elastomeric material, such as a plug or patch 432, to the outer surface 436 and/or, preferably to the inner surface 430 of the shell 412, to form a secure seal covering the opening 420. As in previous examples, the chamber of the implant can be filled with a liquid, such as saline, or with a cohesive gel 434 which, when cured, adheres to the textured inner surface 430 of the inner zone 424. As previously described, adhesion between the shell 412 and the cohesive gel 434 is enhanced as a result of the increased surface area of the textured inner surface 430 compared to a flat surface enclosing the same volume.

Figure 35A:
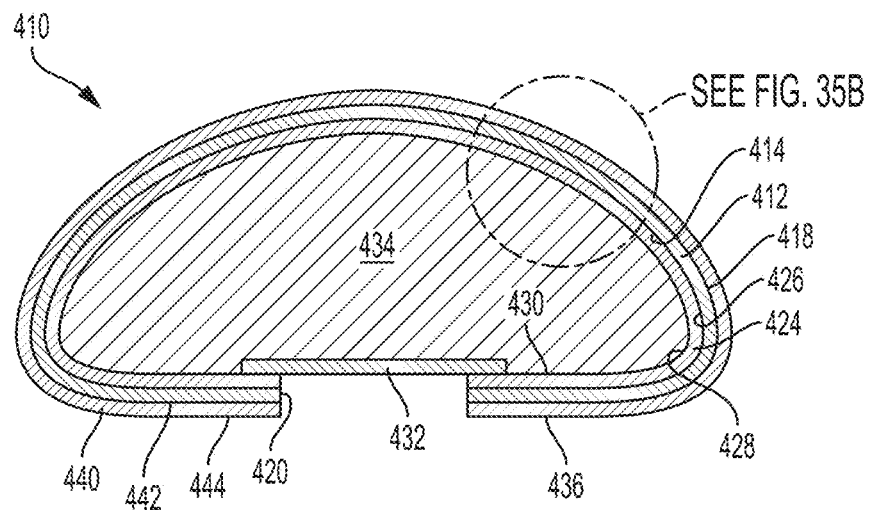
FIGS. 35A and 35B are schematic drawings of a three-zone implant formed by the exemplary process illustrated in FIGS. 34A-34D, according to an aspect of the present disclosure.
Figure 35B:
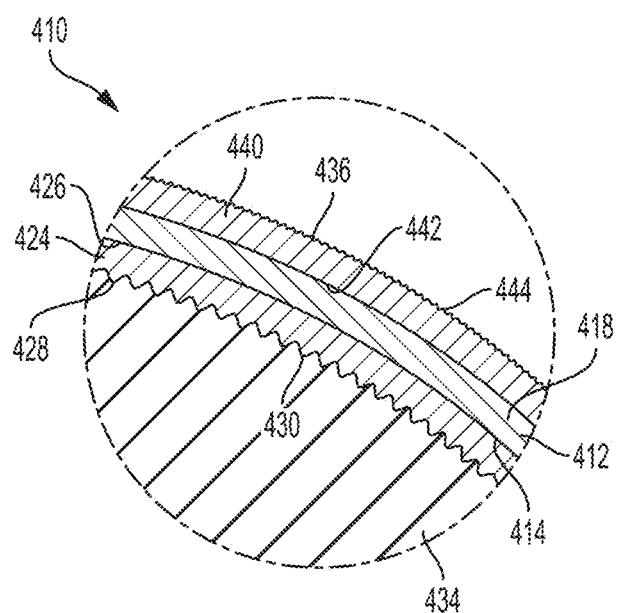

The completed three-zone implant 410 is shown in FIGS. 35A and 35B. The implant 410 includes the enclosed or partially enclosed elastomeric shell 412 and the cohesive gel 434 disposed in an interior of the elastomeric shell 412. As in previous examples, the cohesive gel 434 adheres to the textured inner surface 430 of the shell 412 to provide a stable interface between the shell 412 and gel 434, which reduces a possibility of delamination. The elastomeric shell 412 includes the pre-formed portion or shell 412 comprising at least one elastomeric layer. The elastomeric shell 412 also includes the outer zone 440 and inner zone 424. As described above, in the completed implant 410, layers of the outer zone 440 and the inner zone 424 are forced to conform to a reduced volume, which is less than a volume enclosed by the inner zone 424 and/or the outer zone 440 when cured. As a result of the retraction of the outer zone 440 and compression of the inner zone 424, the inner surface 430 and the outer surface 436 of the implant shell 412 are textured. The textured surfaces 430, 436 are shown, for example, in FIG. 35B and in the photographs of FIGS. 36A and 36B. The cohesive gel 434 is configured to adhere to the textured surface 430 of the inner zone 424 to form a stable interface between the cohesive gel 434 and inner zone 424. In a similar manner, the textured outer surface 436 provides enhanced adhesion between the implant 410 and biological tissues, such as breast tissues, which can improve surgical outcomes. For example, as a result of the textured outer surface 436, the implant 410 can be more securely anchored within biological tissue.

Figure 36A:
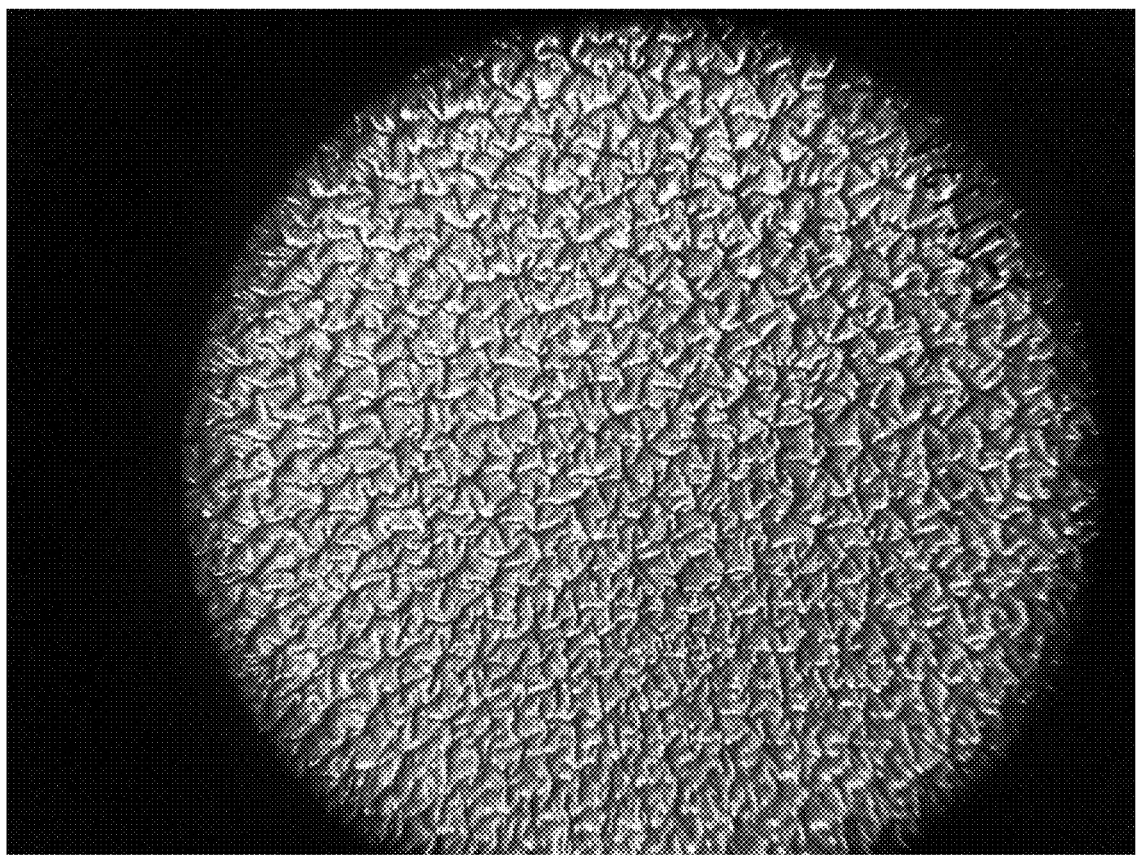
FIG. 36A is a photograph of an inner surface of an implant shell formed according to the process of FIGS. 33A-33E or FIGS. 34A-34D.
Figure 36B:
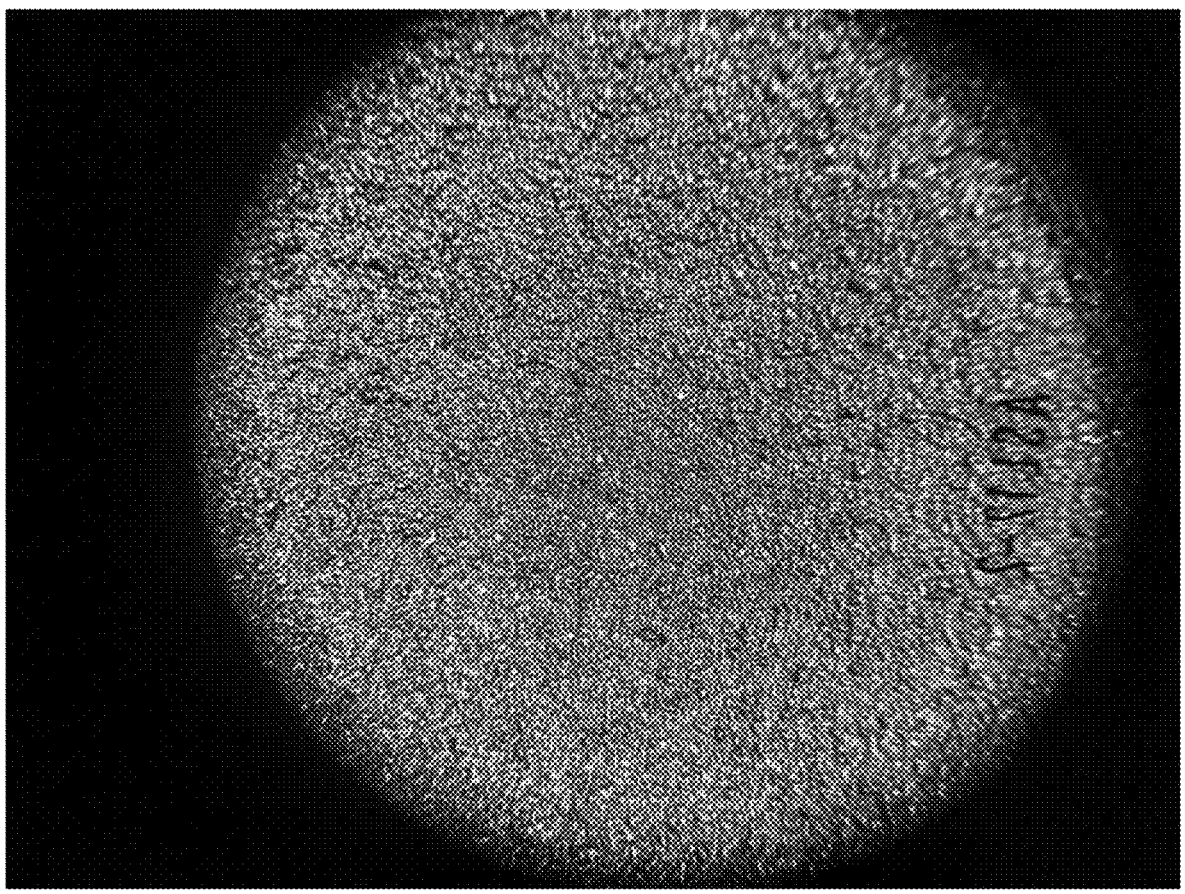
FIG. 36B is a photograph of an outer surface of an implant shell formed according to the process of FIGS. 34A-34D.

Surfaces having different degrees of texturing, such as different sizes of folds or depths of crevices, can be formed by using materials of differing hardness and/or based on an amount of retraction and compression of the layers. While many different arrangements are possible, generally, the softer inner zone 434 will have larger folds, to provide additional surface area for promoting adhesion between the cohesive gel 434 and inner surface 430 of the shell 412. A photograph of an exemplary inner surface 430 including large folds is shown in FIG. 36A. Generally, the textured surface 436 of the outer zone 440 has a more granular appearance with a larger number of smaller folds. A photograph of an exemplary outer surface 436 is shown in FIG. 36B.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

The invention claimed is:

1. A method of forming an implant for volumetrically altering, replacing, expanding, or augmenting body tissues, the method comprising:
   providing a preformed shell formed from at least one cured elastomeric layer, the preformed shell comprising an outer surface, an inner surface, and an opening for accessing an interior volume of the preformed shell;
   expanding the preformed shell to an expanded state, in which the interior volume is greater than the interior volume of the preformed shell at a time of forming the preformed shell;
   forming an inner zone comprising at least one inner elastomeric layer on at least a portion of the inner surface of the preformed shell, while the shell is in the expanded state, thereby forming a multi-zone shell;
   reducing the interior volume of the multi-zone shell, thereby contracting the at least one inner elastomeric layer of the inner zone and causing texturing of the at least one inner elastomeric layer; and
   forming the implant by enclosing the multi-zone shell to form at least one chamber.

2. The method of claim 1, wherein expanding the preformed shell to the expanded state comprises inverting the preformed shell and placing the inverted preformed shell on a mandrel, such that the outer surface of the shell contacts a surface of the mandrel.

3. The method of claim 2, wherein a volume enclosed by the surface of the mandrel is greater than the interior volume of the preformed shell at the time of forming the preformed shell.

4. The method of claim 2, wherein reducing the interior volume of the multi-zone shell comprises removing the multi-zone shell from the mandrel and returning the multi-zone shell to a non-inverted orientation.

5. The method of claim 1, wherein expanding the preformed shell comprises expanding the interior volume of the preformed shell by between 50% and 800% compared to the volume of the preformed shell at the time of forming the preformed shell.

6. The method of claim 1, wherein forming the inner zone comprises, while the preformed shell is in the expanded state, forming a plurality of laminated inner elastomeric layers of variable hardness on the inner surface of the preformed shell.

7. The method of claim 6, wherein a proximal-most layer of the plurality of inner elastomeric layers and a distal-most layer of the plurality of inner elastomeric layers are firmer than middle layers of the plurality of laminated inner elastomeric layers.

8. The method of claim 7, wherein the proximal-most layer and the distal-most layer of the plurality of inner elastomeric layers are formed by blending elastomeric materials having a hardness of up to Shore A-20, and wherein the middle layers of the plurality of inner elastomeric layers have a hardness of between about Shore 00-10 and Shore A-10.

9. The method of claim 1, wherein forming the implant comprising filling the interior volume of the multi-zone shell with a flowable elastomeric material and curing the flowable elastomeric material to form a cohesive gel.

10. The method of claim 9, wherein the cohesive gel is bonded to the texturing of the at least one inner elastomeric layer.

11. The method of claim 10, wherein a volume of the cohesive gel when cured is between about 5% and 50% larger than a volume enclosed by the preformed shell at the time of forming the preformed shell.

12. The method of claim 1, further comprising forming an outer zone comprising at least one outer elastomeric layer covering at least a portion of the outer surface of the preformed shell, while the preformed shell is in the expanded state and prior to forming the inner zone.

13. The method of claim 12, further comprising reducing the interior volume of the preformed shell after forming the outer zone, which causes texturing of the at least one outer elastomeric layer of the outer zone.

14. The method of claim 13, wherein the texturing of the outer zone is configured to provide an adhesion region for improving adhesion with surrounding body tissues.

15. The method of claim 12, wherein the outer zone comprises a plurality of outer elastomeric layers of variable hardness ranging from about Shore 00-30 to Shore A-20.

16. The method of claim 12, wherein forming the outer zone comprises placing the preformed shell on a mandrel, such that the inner surface of the preformed shell contacts the surface of the mandrel, and applying the at least one outer elastomeric layer to the outer surface of the preformed shell.

17. The method of claim 16, wherein a volume enclosed by the mandrel is greater than the volume of the preformed shell, at the time of forming the preformed shell.

18. A method of forming an implant for volumetrically altering, replacing, expanding, or augmenting body tissues, the method comprising:
   providing a preformed shell formed from at least one cured elastomeric layer, the preformed shell comprising an outer surface, an inner surface, and an opening for accessing an interior volume of the preformed shell;
   placing the preformed shell on a mandrel to expand the preformed shell to an expanded state in which the interior volume of the preformed shell is greater than a volume of the preformed shell at a time of forming the preformed shell;
   while the preformed shell is on the mandrel, forming an outer zone comprising at least one outer elastomeric layer on at least a portion of the outer surface of the preformed shell, while the preformed shell is in the expanded state, to form a multi-zone shell;
   placing the multi-zone shell on the mandrel in an inverted orientation, in which the outer zone of the multi-zone shell contacts the mandrel;
   forming an inner zone comprising at least one inner elastomeric layer on at least a portion of the inner surface of the multi-zone shell, while the multi-zone shell is on the mandrel and in the expanded state;
   reducing the interior volume of the multi-zone shell by removing the multi-zone shell from the mandrel, thereby contracting the at least one outer elastomeric layer and the at least one inner elastomeric layer, and causing texturing of the at least one outer elastomeric layer and the at least one inner elastomeric layer; and forming the implant by enclosing the shell to form at least one chamber.

19. An implant for volumetrically altering, replacing, expanding, or augmenting tissues, comprising:

an enclosed or partially enclosed elastomeric shell formed from a plurality of laminated elastomeric layers, the elastomeric shell defining an interior volume; and a cohesive gel disposed in the interior volume of the elastomeric shell, wherein the elastomeric shell comprises:

a preformed shell comprising at least one elastomeric layer, the preformed shell having an inner surface and an outer surface;

an outer zone comprising at least one outer elastomeric layer covering at least a portion of the outer surface of the preformed shell; and an inner zone comprising at least one inner elastomeric layer covering at least a portion of the inner surface of the preformed shell, wherein a volume enclosed by the outer zone and the inner zone at the time of forming the outer zone and the inner zone is greater than a volume of the preformed shell at a time of forming the preformed shell.

20. The implant of claim 19, wherein the volume enclosed by the outer zone and the inner zone of the implant is less than the volume enclosed by the outer zone and the inner zone at the time of forming the outer zone and the inner zone, such that the preformed shell exerts a contracting force on the inner zone and the outer zone, which causes texturing of the inner zone and the outer zone.

* * * * *